United States Patent
Serrano Carmona

(10) Patent No.: US 10,449,371 B2
(45) Date of Patent: Oct. 22, 2019

(54) PATIENT-GUIDED PROGRAMMING ALGORITHMS AND USER INTERFACES FOR NEUROSTIMULATOR PROGRAMMING

(71) Applicant: Boston Scientific Neuromodulation Corporation, Valencia, CA (US)

(72) Inventor: Raul Enrique Serrano Carmona, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/674,008

(22) Filed: Aug. 10, 2017

(65) Prior Publication Data

US 2018/0043172 A1 Feb. 15, 2018

Related U.S. Application Data

(60) Provisional application No. 62/375,185, filed on Aug. 15, 2016.

(51) Int. Cl.
*A61N 1/372* (2006.01)
*A61B 5/00* (2006.01)
(Continued)

(52) U.S. Cl.
CPC ........ *A61N 1/37247* (2013.01); *A61B 5/4848* (2013.01); *A61N 1/0551* (2013.01);
(Continued)

(58) Field of Classification Search
CPC .. A61N 1/00; A61N 1/36071; A61N 1/37247; A61N 1/36; A61N 1/36182; A61N 1/0551; A61N 1/36185; G06F 19/00
(Continued)

(56) References Cited

U.S. PATENT DOCUMENTS

2004/0034394 A1* 2/2004 Woods ............... A61N 1/37247
607/46
2004/0215286 A1 10/2004 Stypulkowski
(Continued)

FOREIGN PATENT DOCUMENTS

WO WO-2017053237 A1 3/2017
WO WO-2018034940 A1 2/2018

OTHER PUBLICATIONS

"Patient Programmer—Medtronic DBS Therapy user manual 37642", Medtronic, (2015), 149 pgs.
(Continued)

*Primary Examiner* — Jon Eric C Morales
(74) *Attorney, Agent, or Firm* — Schwegman Lundberg & Woessner, P.A.

(57) ABSTRACT

An example of a system may include a processor and a memory device comprising instructions, which when executed by the processor, cause the processor to generate a user interface to receive a therapy efficacy indication from a human subject for an neurostimulation treatment, receive user input in the user interface to select a therapy efficacy indication of the neurostimulation treatment, and identify a modification to a neurostimulation program based on the user input. For example, a therapy efficiency indication received in the user interface may indicate a perceived stimulation intensity, a perceived pain level, and a perceived location characteristic of the neurostimulation treatment. Based on the therapy efficacy indication and other user input in the graphical user interface, an updated setting to modify a parameter setting and implement a change to the neurostimulation treatment with a neurostimulation device can be provided.

20 Claims, 10 Drawing Sheets

(51) Int. Cl.
*A61N 1/05* (2006.01)
*A61N 1/36* (2006.01)

(52) U.S. Cl.
CPC ..... *A61N 1/36071* (2013.01); *A61N 1/36132* (2013.01); *A61N 1/36062* (2017.08)

(58) Field of Classification Search
USPC .......................................................... 607/46
See application file for complete search history.

(56) References Cited

U.S. PATENT DOCUMENTS

| | | | |
|---|---|---|---|
| 2007/0265681 A1* | 11/2007 | Gerber | A61N 1/36071 607/46 |
| 2008/0027514 A1 | 1/2008 | DeMulling et al. | |
| 2010/0010589 A1 | 1/2010 | Skelton | |
| 2010/0280440 A1 | 11/2010 | Skelton et al. | |
| 2015/0151125 A1* | 6/2015 | Zhu | A61N 1/36071 607/46 |
| 2016/0082261 A1 | 3/2016 | Moffitt et al. | |

OTHER PUBLICATIONS

"Precision Plus Spinal Cord Stimulator System—Remote Control Quck Start Guide (Model SC-5212)", Boston Scientific, (2014), 2 pgs.

"Precision Spectra Spinal Cord Stimulator System—Remote Control Quick Start Guide (Model SC-5232)", Boston Scientific, (2014), 2 pgs.

"StimRouter Neuromodulation System—Clinician's Guide", Bioness, (2016), 98 pgs.

"International Application Serial No. PCT/US2017/046302, International Search Report dated Nov. 7, 2017", 7 pgs.

"International Application Serial No. PCT/US2017/046302, Written Opinion dated Nov. 7, 2017", 9 pgs.

* cited by examiner

PATIENT-GUIDED PROGRAMMING ALGORITHMS AND USER INTERFACES FOR NEUROSTIMULATOR PROGRAMMING

CLAIM OF PRIORITY

This application claims the benefit of priority under 35 U.S.C. § 119(e) of U.S. Provisional Patent Application Ser. No. 62/375,185, filed on Aug. 15, 2016, which is herein incorporated by reference in its entirety.

TECHNICAL FIELD

The present disclosure relates generally to medical devices, and more particularly, to systems, devices, and methods for electrical stimulation programming techniques.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is commonly used to program the implantable neurostimulator with stimulation parameters controlling the delivery of the neurostimulation energy.

While modern electronics can accommodate the need for generating stimulation energy, the capability of a neurostimulation system depends on its post-manufacturing programmability to a great extent. For example, a sophisticated neurostimulation program may only benefit a patient when it is customized for that patient, and stimulation patterns or programs of patterns that are predetermined at the time of manufacturing may substantially limit the potential for the customization. Limited types of customization can be performed for the patient in a clinical setting, but the patient may desire additional changes to the location, intensity, duration, or type of stimulation after the clinical encounter.

SUMMARY

Example 1 is a system, comprising: a processor; and a memory device comprising instructions, which when executed by the processor, cause the processor to perform operations that: generate a user interface to receive a therapy efficacy indication from a human subject for an neurostimulation treatment provided to the human subject, wherein the neurostimulation treatment is provided to the human subject from a neurostimulation device operating with a program of a plurality of programmable parameter settings; receive user input in the user interface from the human subject, wherein the user input corresponds to a selection of the therapy efficacy indication from among a plurality of selectable indications output in the user interface; identify, based on the therapy efficacy indication selected in the user interface, a modification to the program, wherein the modification to the program provides an updated setting for at least one of the plurality of programmable parameter settings; and transmit, to the neurostimulation device, the updated setting for the at least one of the plurality of programmable parameter settings, wherein the neurostimulation device modifies the program and implements a change to the neurostimulation treatment in response to receipt of the updated setting; wherein the therapy efficacy indication received from the human subject indicates a perceived stimulation intensity, a perceived pain level, and a perceived location characteristic of the neurostimulation treatment, as perceived by the human subject.

In Example 2, the subject matter of Example 1 optionally includes, instructions further to cause the processor to: receive user input in the user interface to accept the modification to the program, wherein the modification to the program is persisted to the neurostimulation device in response to the user input to accept the modification.

In Example 3, the subject matter of any one or more of Examples 1-2 optionally include: the therapy efficacy indication received from the human subject indicates that the neurostimulation treatment is not in proximity to a desired location; wherein the operations to identify the modification to the program include: identification of a central point of stimulation based on a pain area of the human subject and therapy characteristics for treatment of the pain area; and identification of a midline for stimulation in the pain area; wherein the modification to the program uses the updated setting to move the neurostimulation treatment to a location corresponding to the central point of stimulation and the midline for stimulation; wherein the instructions further cause the processor to perform operations that: receive user input in the user interface to select a subsequent therapy efficacy indication, wherein the subsequent therapy efficacy indication received from the human subject indicates at least one of: a subsequent perceived stimulation intensity, a subsequent perceived pain level, and a subsequent perceived location characteristic of the neurostimulation treatment, as perceived by the human subject for the modification to the program; identify, based on the subsequent therapy efficacy indication selected in the user interface, a subsequent modification to the program, wherein the subsequent modification causes a change to a location of the neurostimulation treatment based on the midline for stimulation in the pain area; and repeat operations to receive the subsequent therapy efficacy indication and identify the subsequent modification to the program, until acceptance of the subsequent modification to the program by the human subject.

In Example 4, the subject matter of any one or more of Examples 1-3 optionally include: the therapy efficacy indication received from the human subject indicates that the neurostimulation treatment is in proximity to a desired location; wherein the operations to identify the modification to the program include: identification of a central point of stimulation using electrode fractionalization; wherein the modification to the program provides the updated setting for at least one of the plurality of programmable parameter settings to move the neurostimulation treatment to a location corresponding to the central point of stimulation; and wherein the instructions further cause the processor to: receive user input in the user interface to select a subsequent therapy efficacy indication, wherein the subsequent therapy efficacy indication received from the human subject indicates at least one of: a subsequent perceived stimulation intensity, a subsequent perceived pain level, and a subsequent perceived location characteristic of the neurostimulation treatment, as perceived by the human subject for the modification to the program; identify, based on the subsequent therapy efficacy indication selected in the user interface, a subsequent modification to the program, wherein the subsequent modification causes a change to a location of the neurostimulation treatment based on the central point of stimulation; and repeat operations to receive the subsequent therapy efficacy indication and identify the subsequent modification until acceptance of the subsequent modification to the program by the human subject.

In Example 5, the subject matter of any one or more of Examples 1-4 optionally include, instructions further to cause the processor to: receive user input in the user interface to reject the modification to the program; identify a rollback of the modification to the program, wherein the rollback of the modification to the program provides a further updated setting for the at least one of the plurality of programmable parameter settings; and transmit, to the neurostimulation device, the further updated setting that corresponds to the rollback of the modification to the program; wherein the rollback of the modification to the program is applied to the neurostimulation device in response to the user input to reject the modification to the program.

In Example 6, the subject matter of any one or more of Examples 1-5 optionally include: the plurality of programmable parameter settings include settings for one or more of: pulse patterns, pulse shapes, a spatial location of pulses, waveform shapes, or a spatial location of waveform shapes, for modulated energy provided with a plurality of leads of the neurostimulation device.

In Example 7, the subject matter of Example 6 optionally includes: the plurality of programmable parameter settings include settings for two or more of: a frequency, a pulse width, a number of pulses within a burst or train of pulses, a train-to-train interval, a burst frequency of trains of pulses, a pulse duty cycle, or a burst duty cycle, of pulses of modulated energy provided with the plurality of leads of the neurostimulation device.

In Example 8, the subject matter of any one or more of Examples 1-7 optionally include, instructions further to cause the processor to: receive additional user input in the user interface, wherein the additional user input corresponds to an additional selection of an additional therapy efficacy indication by the human subject from among the plurality of selectable indications presented in the user interface, wherein the additional selection of the therapy efficacy indication is provided by the human subject in response to the change to the neurostimulation treatment; identify, based on the therapy efficacy indication selected in the user interface, a subsequent updated setting for the at least one of the plurality of programmable parameter settings; and transmit, to the neurostimulation device, the subsequent updated setting for the at least one of the plurality of programmable parameter settings, wherein the neurostimulation device modifies the program and implements a change to the neurostimulation treatment in response to receipt of the subsequent updated setting.

In Example 9, the subject matter of any one or more of Examples 1-8 optionally include, instructions further to cause the processor to: receive additional user input in the user interface, wherein the additional user input corresponds to an additional selection of an additional therapy efficacy indication by the human subject from among the plurality of selectable indications presented in the user interface, wherein the additional selection of the therapy efficacy indication is provided by the human subject in response to the change to the neurostimulation treatment; identify, based on the therapy efficacy indication selected in the user interface, a subsequent program of the plurality of programmable parameter settings; and transmit, to the neurostimulation device, the subsequent program of the plurality of programmable parameter settings, wherein the neurostimulation device implements a change to the neurostimulation treatment using the subsequent program in response to receipt of the subsequent program.

In Example 10, the subject matter of any one or more of Examples 1-9 optionally include: a display screen to generate output of the user interface; and an input device to receive input of the user interface; wherein the user interface is a graphical user interface; wherein the user interface includes inputs to select an indication of the perceived feeling of the neurostimulation treatment, an indication of the perceived location of the neurostimulation treatment, and an indication of the perceived pain level from the neurostimulation treatment; and wherein the user interface further includes a selectable input to reset the modifications to the neurostimulation treatment to a prior setting, and a selectable input to stop the modifications to the neurostimulation treatment.

In Example 11, the subject matter of Example 10 optionally includes: a wireless transceiver to wirelessly communicate data with a programming device; wherein the processor, the memory device, the display screen, and the input device are included in a mobile computing device operated by the human subject; wherein the display screen and the input device are provided in a touchscreen of the mobile computing device; and wherein the modification to the program is communicated via the wireless transceiver to the programming device, wherein the programming device is to communicate the modification to the neurostimulation device.

In Example 12, the subject matter of Example 11 optionally includes: the graphical user interface is a software app adapted for native execution by an operating system of the mobile computing device, and wherein the graphical user interface provides an input display to receive a graphical selection of the therapy efficacy indication by the human subject, and wherein the graphical user interface further provides an output display to output a representation of the modifications to the neurostimulation treatment.

In Example 13, the subject matter of any one or more of Examples 10-12 optionally include: a wireless transceiver to wirelessly communicate data with the neurostimulation device; wherein the processor, the memory device, the display screen, and the input device are included in a programming device operable by the human subject; and wherein, in response to the input, the processor of the programming device is further to: transmit the modification to the program to the neurostimulation device via the wireless transceiver.

Example 14 is a machine-readable medium including instructions, which when executed by a machine, cause the machine to perform the operations of the system of any of the Examples 1 to 13.

Example 15 is a method to perform the operations of the system of any of the Examples 1 to 13.

Example 16 is a device, comprising: user interface processing circuitry, implemented with a processor and a memory, the user interface processing circuitry to perform electronic operations with the device to: generate a user interface to receive a therapy efficacy indication from a human subject for an neurostimulation treatment provided to the human subject, wherein the neurostimulation treatment is provided to the human subject from a neurostimulation device operating with a program of a plurality of programmable parameter settings; receive user input in the user interface from the human subject, wherein the user input corresponds to a selection of the therapy efficacy indication from among a plurality of selectable indications output in the user interface; identify, based on the therapy efficacy indication selected in the user interface, a modification to the program, wherein the modification to the program provides an updated setting for at least one of the plurality of programmable parameter settings; and transmit, to the neurostimulation device, the updated setting for the at least one of the plurality of programmable parameter settings, wherein the neurostimulation device modifies the program and implements a change to the neurostimulation treatment in response to receipt of the updated setting; wherein the therapy efficacy indication received from the human subject indicates a perceived stimulation intensity, a perceived pain level, and a perceived location characteristic of the neurostimulation treatment, as perceived by the human subject.

In Example 17, the subject matter of Example 16 optionally includes: the user interface processing circuitry to further perform electronic operations with the device to: receive user input in the user interface to accept the modification to the program, wherein the modification to the program is persisted to the neurostimulation device in response to the user input to accept the modification.

In Example 18, the subject matter of any one or more of Examples 16-17 optionally include: the therapy efficacy indication received from the human subject indicates that the neurostimulation treatment is not in proximity to a desired location; and wherein the operations to identify the modification to the program include: identification of a central point of stimulation based on a pain area of the human subject and therapy characteristics for treatment of the pain area; and identification of a midline for stimulation in the pain area; wherein the modification to the program uses the updated setting to move the neurostimulation treatment to a location corresponding to the central point of stimulation and the midline for stimulation.

In Example 19, the subject matter of Example 18 optionally includes: the user interface processing circuitry to further perform electronic operations with the device to: receive user input in the user interface to select a subsequent therapy efficacy indication, wherein the subsequent therapy efficacy indication received from the human subject indicates at least one of: a subsequent perceived stimulation intensity, a subsequent perceived pain level, and a subsequent perceived location characteristic of the neurostimulation treatment, as perceived by the human subject for the modification to the program; identify, based on the subsequent therapy efficacy indication selected in the user interface, a subsequent modification to the program, wherein the subsequent modification causes a change to a location of the neurostimulation treatment based on the midline for stimulation in the pain area; and repeat operations to receive the subsequent therapy efficacy indication and identify the subsequent modification to the program, until acceptance of the subsequent modification to the program by the human subject.

In Example 20, the subject matter of any one or more of Examples 16-19 optionally include: the therapy efficacy indication received from the human subject indicates that the neurostimulation treatment is in proximity to a desired location; and wherein the operations to identify the modification to the program include: identification of a central point of stimulation using electrode fractionalization; wherein the modification to the program provides the updated setting for at least one of the plurality of programmable parameter settings to move the neurostimulation treatment to a location corresponding to the central point of stimulation.

In Example 21, the subject matter of Example 20 optionally includes: the user interface processing circuitry to further perform electronic operations with the device to: receive user input in the user interface to select a subsequent therapy efficacy indication, wherein the subsequent therapy efficacy indication received from the human subject indicates at least one of: a subsequent perceived stimulation intensity, a subsequent perceived pain level, and a subsequent perceived location characteristic of the neurostimulation treatment, as perceived by the human subject for the modification to the program; identify, based on the subsequent therapy efficacy indication selected in the user interface, a subsequent modification to the program, wherein the subsequent modification causes a change to a location of the neurostimulation treatment based on the central point of stimulation; and repeat operations to receive the subsequent therapy efficacy indication and identify the subsequent modification until acceptance of the subsequent modification to the program by the human subject.

In Example 22, the subject matter of any one or more of Examples 16-21 optionally include: the user interface processing circuitry to further perform electronic operations with the device to: receive user input in the user interface to reject the modification to the program; identify a rollback of the modification to the program, wherein the rollback of the modification to the program provides a further updated setting for the at least one of the plurality of programmable parameter settings; and transmit, to the neurostimulation device, the further updated setting that corresponds to the rollback of the modification to the program; wherein the rollback of the modification to the program is applied to the neurostimulation device in response to the user input to reject the modification to the program.

In Example 23, the subject matter of any one or more of Examples 16-22 optionally include: the plurality of programmable parameter settings include settings for one or more of: pulse patterns, pulse shapes, a spatial location of pulses, waveform shapes, or a spatial location of waveform shapes, for modulated energy provided with a plurality of leads of the neurostimulation device.

In Example 24, the subject matter of Example 23 optionally includes: the plurality of programmable parameter settings include settings for two or more of: a frequency, a pulse width, a number of pulses within a burst or train of pulses, a train-to-train interval, a burst frequency of trains of pulses, a pulse duty cycle, or a burst duty cycle, of pulses of modulated energy provided with the plurality of leads of the neurostimulation device.

In Example 25, the subject matter of any one or more of Examples 16-24 optionally include: the user interface processing circuitry to further perform electronic operations with the device to: receive additional user input in the user interface, wherein the additional user input corresponds to an additional selection of an additional therapy efficacy indication by the human subject from among the plurality of selectable indications presented in the user interface, wherein the additional selection of the therapy efficacy indication is provided by the human subject in response to the change to the neurostimulation treatment; identify, based on the therapy efficacy indication selected in the user interface, a subsequent updated setting for the at least one of the plurality of programmable parameter settings; and transmit, to the neurostimulation device, the subsequent updated setting for the at least one of the plurality of programmable parameter settings, wherein the neurostimulation device modifies the program and implements a change to the neurostimulation treatment in response to receipt of the subsequent updated setting.

In Example 26, the subject matter of any one or more of Examples 16-25 optionally include: the user interface processing circuitry to further perform electronic operations with the device to: receive additional user input in the user interface, wherein the additional user input corresponds to an additional selection of an additional therapy efficacy indication by the human subject from among the plurality of selectable indications presented in the user interface, wherein the additional selection of the therapy efficacy indication is provided by the human subject in response to the change to the neurostimulation treatment; identify, based on the therapy efficacy indication selected in the user interface, a subsequent program of the plurality of programmable parameter settings; and transmit, to the neurostimulation device, the subsequent program of the plurality of programmable parameter settings, wherein the neurostimulation device implements a change to the neurostimulation treatment using the subsequent program in response to receipt of the subsequent program.

Example 27 is a method, comprising a plurality of electronic operations executed with a processor and memory of a computer system, the plurality of electronic operations including: generating a user interface to receive a therapy efficacy indication from a human subject for an neurostimulation treatment provided to the human subject, wherein the neurostimulation treatment is provided to the human subject from a neurostimulation device operating with a program of a plurality of programmable parameter settings; receiving user input in the user interface from the human subject, wherein the user input corresponds to a selection of the therapy efficacy indication from among a plurality of selectable indications output in the user interface; identifying, based on the therapy efficacy indication selected in the user interface, a modification to the program, wherein the modification to the program provides an updated setting for at least one of the plurality of programmable parameter settings; and transmitting, to the neurostimulation device, the updated setting for the at least one of the plurality of programmable parameter settings, wherein the neurostimulation device modifies the program and implements a change to the neurostimulation treatment in response to receipt of the updated setting; wherein the therapy efficacy indication received from the human subject indicates a perceived stimulation intensity, a perceived pain level, and a perceived location characteristic of the neurostimulation treatment, as perceived by the human subject.

In Example 28, the subject matter of Example 27 optionally includes: receiving user input in the user interface to accept the modification to the program, wherein the modification to the program is persisted to the neurostimulation device in response to the user input to accept the modification.

In Example 29, the subject matter of any one or more of Examples 27-28 optionally include, the therapy efficacy indication received from the human subject indicates that the neurostimulation treatment is not in proximity to a desired location; and wherein the identifying the modification to the program includes: identification of a central point of stimulation based on a pain area of the human subject and therapy characteristics for treatment of the pain area; and identification of a midline for stimulation in the pain area; wherein the modification to the program uses the updated setting to move the neurostimulation treatment to a location corresponding to the central point of stimulation and the midline for stimulation.

In Example 30, the subject matter of Example 29 optionally includes: receiving user input in the user interface to select a subsequent therapy efficacy indication, wherein the subsequent therapy efficacy indication received from the human subject indicates at least one of: a subsequent perceived stimulation intensity, a subsequent perceived pain level, and a subsequent perceived location characteristic of the neurostimulation treatment, as perceived by the human subject for the modification to the program; identifying, based on the subsequent therapy efficacy indication selected in the user interface, a subsequent modification to the program, wherein the subsequent modification causes a change to a location of the neurostimulation treatment based on the midline for stimulation in the pain area; and repeating operations to receive the subsequent therapy efficacy indication and identify the subsequent modification to the program, until acceptance of the subsequent modification to the program by the human subject.

In Example 31, the subject matter of any one or more of Examples 27-30 optionally include, the therapy efficacy indication received from the human subject indicates that the neurostimulation treatment is in proximity to a desired location; wherein identifying the modification to the program includes: identification of a central point of stimulation using electrode fractionalization; wherein the modification to the program provides the updated setting for at least one of the plurality of programmable parameter settings to move the neurostimulation treatment to a location corresponding to the central point of stimulation.

In Example 32, the subject matter of Example 31 optionally includes: receiving user input in the user interface to select a subsequent therapy efficacy indication, wherein the subsequent therapy efficacy indication received from the human subject indicates at least one of: a subsequent perceived stimulation intensity, a subsequent perceived pain level, and a subsequent perceived location characteristic of the neurostimulation treatment, as perceived by the human subject for the modification to the program; identifying, based on the subsequent therapy efficacy indication selected in the user interface, a subsequent modification to the program, wherein the subsequent modification causes a change to a location of the neurostimulation treatment based on the central point of stimulation; and repeating operations to receive the subsequent therapy efficacy indication and identify the subsequent modification until acceptance of the subsequent modification to the program by the human subject.

In Example 33, the subject matter of any one or more of Examples 27-32 optionally include: receiving user input in the user interface to reject the modification to the program; identifying a rollback of the modification to the program, wherein the rollback of the modification to the program provides a further updated setting for the at least one of the plurality of programmable parameter settings; and transmitting, to the neurostimulation device, the further updated setting that corresponds to the rollback of the modification to the program; wherein the rollback of the modification to the program is applied to the neurostimulation device in response to the user input to reject the modification to the program.

In Example 34, the subject matter of any one or more of Examples 27-33 optionally include: the plurality of programmable parameter settings include settings for one or more of: pulse patterns, pulse shapes, a spatial location of pulses, waveform shapes, or a spatial location of waveform shapes, for modulated energy provided with a plurality of leads of the neurostimulation device.

In Example 35, the subject matter of Example 34 optionally includes: the plurality of programmable parameter settings include settings for two or more of: a frequency, a pulse width, a number of pulses within a burst or train of pulses, a train-to-train interval, a burst frequency of trains of pulses, a pulse duty cycle, or a burst duty cycle, of pulses of modulated energy provided with the plurality of leads of the neurostimulation device.

In Example 36, the subject matter of any one or more of Examples 27-35 optionally include: receiving additional user input in the user interface, wherein the additional user input corresponds to an additional selection of an additional therapy efficacy indication by the human subject from among the plurality of selectable indications presented in the user interface, wherein the additional selection of the therapy efficacy indication is provided by the human subject in response to the change to the neurostimulation treatment; identifying, based on the therapy efficacy indication selected in the user interface, a subsequent updated setting for the at least one of the plurality of programmable parameter settings; and transmitting, to the neurostimulation device, the subsequent updated setting for the at least one of the plurality of programmable parameter settings, wherein the neurostimulation device modifies the program and implements a change to the neurostimulation treatment in response to receipt of the subsequent updated setting.

In Example 37, the subject matter of any one or more of Examples 27-36 optionally include: receiving additional user input in the user interface, wherein the additional user input corresponds to an additional selection of an additional therapy efficacy indication by the human subject from among the plurality of selectable indications presented in the user interface, wherein the additional selection of the therapy efficacy indication is provided by the human subject in response to the change to the neurostimulation treatment; identifying, based on the therapy efficacy indication selected in the user interface, a subsequent program of the plurality of programmable parameter settings; and transmitting, to the neurostimulation device, the subsequent program of the plurality of programmable parameter settings, wherein the neurostimulation device implements a change to the neurostimulation treatment using the subsequent program in response to receipt of the subsequent program.

Example 38 is an apparatus comprising means for performing any of the methods of Examples 27-37.

Example 39 is a non-transitory machine-readable medium including instructions, which when executed by a machine, cause the machine to: generate a user interface to receive a therapy efficacy indication from a human subject for an neurostimulation treatment provided to the human subject, wherein the neurostimulation treatment is provided to the human subject from a neurostimulation device operating with a program of a plurality of programmable parameter settings; receive user input in the user interface from the human subject, wherein the user input corresponds to a selection of the therapy efficacy indication from among a plurality of selectable indications output in the user interface; identify, based on the therapy efficacy indication selected in the user interface, a modification to the program, wherein the modification to the program provides an updated setting for at least one of the plurality of programmable parameter settings; and transmit, to the neurostimulation device, the updated setting for the at least one of the plurality of programmable parameter settings, wherein the neurostimulation device modifies the program and implements a change to the neurostimulation treatment in response to receipt of the updated setting; wherein the therapy efficacy indication received from the human subject indicates a perceived stimulation intensity, a perceived pain level, and a perceived location characteristic of the neurostimulation treatment, as perceived by the human subject.

Example 40 is an apparatus, comprising: means for generating a user interface to receive a therapy efficacy indication from a human subject for an neurostimulation treatment provided to the human subject, wherein the neurostimulation treatment is provided to the human subject from a neurostimulation device operating with a program of a plurality of programmable parameter settings; means for receiving user input in the user interface from the human subject, wherein the user input corresponds to a selection of the therapy efficacy indication from among a plurality of selectable indications output in the user interface; means for identifying, based on the therapy efficacy indication selected in the user interface, a modification to the program, wherein the modification to the program provides an updated setting for at least one of the plurality of programmable parameter settings; and means for transmitting, to the neurostimulation device, the updated setting for the at least one of the plurality of programmable parameter settings, wherein the neurostimulation device modifies the program and implements a change to the neurostimulation treatment in response to receipt of the updated setting; wherein the therapy efficacy indication received from the human subject indicates a perceived stimulation intensity, a perceived pain level, and a perceived location characteristic of the neurostimulation treatment, as perceived by the human subject.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
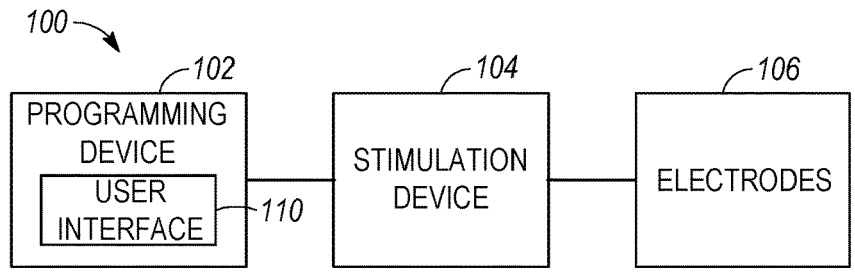
FIG. 1 illustrates, by way of example, an embodiment of a neurostimulation system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

This document discusses various techniques that can allow a user to select, modify, and implement certain programming parameters (e.g., settings) for a neurostimulator, based on the receipt and processing of an efficacy indication (e.g., whether the effect of the neurostimulation therapy is perceived by the patient as satisfactory or improved). Based on user inputs received in a graphical user interface that indicate a selection of one or more efficacy indications, one or more programming parameters may be identified and implemented (or updated) with a neurostimulation device. These programming parameters may be arranged or defined into sets of neurostimulation programs (also plainly referred to as "programs" in this document), and such neurostimulation programs may be modified in response to the selection, receipt, and processing of user inputs corresponding to such efficacy indications.

The techniques of this document can enable a human subject (e.g., patient) to select or modify a program for a device (or to re-program a device) within an iteration of possible programs and program settings, to converge changes to a program based on perceived efficacy. In an example, the modification logic is configured to modify programming parameters and programs of parameters based on the perceived and desired characteristics of treatment, such as stimulation intensity, stimulation location, and resultant pain level, to affect a medical condition with the neurostimulation device. The various techniques are implemented through the use of user interfaces, selection logic, and application interfaces to access, select, retrieve, update, store, and persist parameter settings (or a program of parameters) in the neurostimulation device. This can enable the human subject to effectively re-program the neurostimulator device based on real-time feedback and perceived treatment inputs, particularly when the human subject is not located in a clinical setting and desires changes to his or her treatment.

The system and devices described in this disclosure allow a patient user to modify a particular neurostimulation program or neurostimulation device setting with a user interface, based on user inputs in the user interface that correspond to a perceived efficacy of the neurostimulation treatment. The user inputs may provide one or more values that indicate a perceived strength of treatment (e.g., the treatment feeling weak, feeling strong, or feeling satisfactory), a perceived location of the treatment (e.g., the treatment feeling close or closer to the area of pain, feeling far or farther away from the area of pain, or feeling in a satisfactory location), a perceived comfort or discomfort from the treatment (e.g., stimulation on a non-desirable area, uncomfortable sensations due to stimulation, a user-preferred improvement to the type or intensity of stimulation, etc.), and a perceived pain level in response to the treatment (e.g., the treatment resulting in perceived increased pain, perceived decreased pain, or no perceived change). The user input that is received to identify these characteristics, referred to herein as a "therapy efficacy indication," may be processed with programming modification logic to determine an appropriate change, modification, or result to a program or setting based on the user input. For example, if a patient indicates that the pain is decreasing as a result of a setting change, the programming modification logic may increase the setting change gradually until the pain is perceived by the patient at an acceptable level. Also for example, if a patient indicates that the treatment is not located in a desired area, the programming modification logic may move the location of the treatment gradually until the location is perceived at an acceptable location. This type of adjustment may be performed with a feedback loop, to allow adjustment and feedback for the settings in real time, as the treatment location, intensity, and type are adjusted.

As a result of the programming modification logic and accompanying changes to a neurostimulation program and device settings, the interfaces of the present disclosure can implement granular and discrete control for operational parameters of the neurostimulation device. By way of example, such parameters may include amplitude, frequency, duration, pulse width, pulse type, patterns of neurostimulation pulses, waveforms in the patterns of pulses, and like settings with respect to the intensity, type, and location of neurostimulator output on individual or a plurality of respective leads. The neurostimulator may use current or voltage sources to provide the neurostimulator output, and to provide modified output directly or indirectly in response to the receipt of the therapy efficacy indications in a user interface (e.g., a graphical user interface or a feature-limited device user interface). The features of this user interface, discussed in additional detail below, enable a more precise and focused identification of a program or program setting and the effective use of a neurostimulator program treatment, based on treatment efficacy indications directly received from the human subject.

In various embodiments, a neurostimulator program may include parameters that define spatial, temporal, and informational characteristics for the delivery of modulated energy, including the definitions or parameters of pulses of modulated energy, waveforms of pulses, pulse blocks each including a burst of pulses, pulse trains each including a sequence of pulse blocks, train groups each including a sequence of pulse trains, and programs of such definitions or parameters, each including one or more train groups scheduled for delivery. Characteristics of the waveform that are defined in the program may include, but are not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time). It will be understood that based on the many characteristics of the waveform itself, a program may have many parameter setting combinations that would be potentially available for use. As a result, the present techniques may be used for the modification or selection of a program as a result of a therapy efficacy indication, including one or more starting, initial, default, experimental, recommended, subsequent, or modified programming settings in a clinical setting or post-clinical setting; further, the present techniques may be used by clinicians and professionals to monitor the efficacy of treatment of a particular program or set of program settings as the human subject participates in real-world activities outside of a clinical setting.

In various embodiments, the present subject matter may be implemented using a combination of hardware and software designed to provide users such as patients, caregivers, clinicians, researchers, physicians or others with the ability to select and implement feedback-based modifications to neurostimulation programs. Such modifications may affect the location, intensity, and type of defined waveforms and patterns in an effort to increase therapeutic efficacy and/or patient satisfaction for neurostimulation therapies, including but not being limited to SCS and DBS therapies. While neurostimulation is specifically discussed as an example, the present subject matter may apply to any therapy that employs stimulation pulses of electrical or other forms of energy.

The delivery of neurostimulation energy that is discussed herein may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, neural signals may include more sophisticated patterns to communicate various types of information, including sensations of pain, pressure, temperature, etc.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a clinical user, such as a physician or other caregiver who treats the patient using system 100. Programming device 102 provides the user with accessibility to the user-programmable parameters. In various embodiments, programming device 102 is configured to be communicatively coupled to stimulation device 104 via a wired or wireless link.

In various embodiments, programming device 102 includes a user interface 110 (e.g., a user interface embodied by a graphical, text, voice, or hardware-based user interface) that allows the user to set and/or adjust values of the user-programmable parameters by creating, editing, loading, and removing programs that include parameter combinations such as patterns and waveforms. These adjustments may also include changing and editing values for the user-programmable parameters or sets of the user-programmable parameters individually (including values set in response to a therapy efficacy indication). Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups. The program and respective sets of parameters may also define an electrode selection specific to each individually defined waveform.

As described in more detail below with respect to FIGS. 6 and 7, a user, e.g., the human subject or patient, can select, load, modify, and implement one or more parameters of a defined program for neurostimulation treatment, based on user inputs that correspond to a therapy efficacy indication (e.g., whether the treatment or a change to the treatment is perceived as applied to a correct location, is too strong or weak, or causes an increase or decrease in pain). Based on received user input and the characteristics of the program, the programming device 102 can determine a subset of available electrodes and current distributions for the subset to generate the stimulation output. Example parameters that can be implemented by a program and are modifiable by received user input include, but are not limited to the following: amplitude, pulse width, frequency, duration, total charge injected per unit time, cycling (e.g., on/off time), pulse shape, number of phases, phase order, interphase time, charge balance, ramping, as well as spatial variance (e.g., electrode configuration changes over time).

As also discussed further herein, the user input that provides the therapy efficacy indication can be received in a user interface of another external device (such as a patient feedback computing device, not shown in FIG. 1) or in the user interface 110 of the programming device 102. This user input can be processed by modification logic (not shown in FIG. 1) to implement or modify a program that specifies one or more of these parameters, such as to define at least one of a pulse of the neurostimulation waveform, a pulse group of the neurostimulation waveform, and a group of pulse groups of the neurostimulation waveform, and to modify the virtual location for application of these waveforms, for example. The user input can also be processed by the modification logic to determine customized values for one or more of these parameters, including the amount of change, the direction of a location change, and the type of change to the parameters. For example, the implementation of different spatiotemporal patterns of pulses, waveforms, and the like can be used to induce different sensations (temperature, pressure, pain relief, tingles, etc.) in response to the detection and processing of the therapy efficacy indication.

Figure 6:
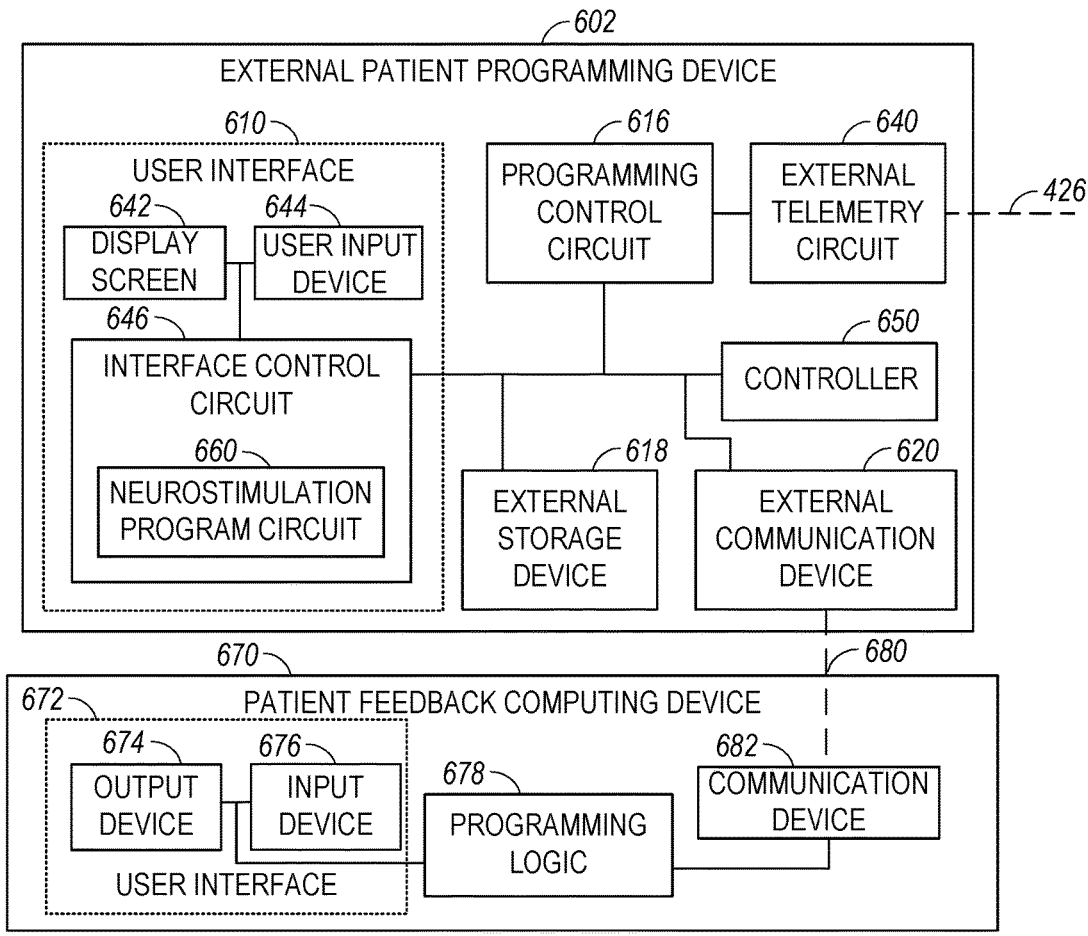
FIG. 6 illustrates, by way of example, an embodiment of a patient feedback computing device and an external programming device for a neurostimulation system, such as the implantable neurostimulation system of FIG. 4.

As detailed in FIG. 6, a controller, e.g., controller 650 of FIG. 6, can implement program(s) and parameter setting(s) to implement a specific neurostimulation waveform, pattern, or energy output, using a program or setting in storage, e.g., external storage device 618 of FIG. 6, or using settings communicated via an external communication device 620 of FIG. 6 from a patient feedback computing device 670 or another external service or device. Such implementation may further define a therapy strength and treatment type corresponding to a specific pulse group, a specific group of pulse groups, and the like, in response to the receipt of the therapy efficacy indication in a user interface. As also described in more detail below with respect to FIG. 6 and thereafter, in some example implementations, the user can obtain or identify a recommended, matching, or corresponding program of parameters from a patient feedback computing device 670 in response to direct input of a therapy efficacy indication value. This guided program of parameters may be selected and implemented with the programming device 102 as a "best match" for initial or updated programming settings of the stimulation device 104, to address the specific medical treatment and treatment objectives for a human subject. As also described, the user can obtain or identify modified settings of a program of parameters from the patient feedback computing device 670 in response to subsequent input of a therapy efficacy indication input (including an indication of whether the treatment has improved or worsened as a result of the program or program setting change).

Portions of the stimulation device 104, e.g., implantable medical device, or the programming device 102 can be implemented using hardware, software, or any combination of hardware and software. Portions of the stimulation device 104 or the programming device 102 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. The system 100 could include a subcutaneous medical device (e.g., subcutaneous ICD, subcutaneous diagnostic device), wearable medical devices (e.g., patch based sensing device), or other external medical devices.

Figure 2:
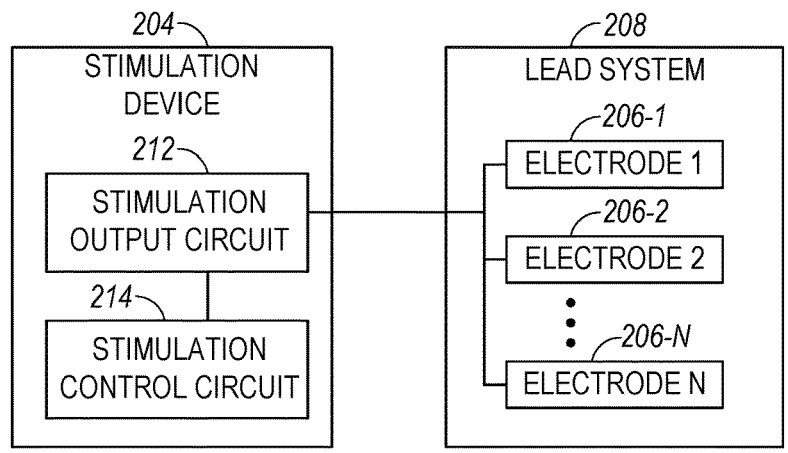
FIG. 2 illustrates, by way of example, an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100 of FIG. 1. Stimulation device 204 represents an embodiment of stimulation device 104 and includes a stimulation output circuit 212 and a stimulation control circuit 214. Stimulation output circuit 212 produces and delivers neurostimulation pulses, including the neurostimulation waveform and parameter settings implemented via a program selected or implemented with the user interface 110. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. Those of ordinary skill in the art will understand that the neurostimulation system 100 may include additional components such as sensing circuitry for patient monitoring and/or feedback control of the therapy, telemetry circuitry, and power.

The neurostimulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter" set. Each set of modulation parameters, including fractionalized current distribution to the electrodes (as percentage cathodic current, percentage anodic current, or off), may be stored and combined into a program that can then be used to modulate multiple regions within the patient.

The neurostimulation system may be configured to deliver different electrical fields to achieve a temporal summation of modulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields can be rotated or cycled through multiple times under a timing scheme, where each field is implemented using a timing channel. The electrical fields may be generated at a continuous pulse rate, or as bursts of pulses. Furthermore, the interpulse interval (i.e., the time between adjacent pulses), pulse amplitude, and pulse duration during the electrical field cycles may be uniform or may vary within the electrical field cycle. Some examples are configured to determine a modulation parameter set to create a field shape to provide a broad and uniform modulation field such as may be useful to prime targeted neural tissue with sub-perception modulation. Some examples are configured to determine a modulation parameter set to create a field shape to reduce or minimize modulation of non-targeted tissue (e.g., dorsal column tissue). Various examples disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of dorsal horn neural tissue and to minimize the modulation of dorsal column tissue. A benefit of MICC is that MICC accounts for various in electrode-tissue coupling efficiency and perception threshold at each individual contact, so that "hotspot" stimulation is eliminated.

The number of electrodes available combined with the ability to generate a variety of complex electrical pulses, presents a huge selection of available modulation parameter sets to the clinician or patient. For example, if the neurostimulation system to be programmed has sixteen electrodes, millions of modulation parameter value combinations may be available for programming into the neurostimulation system. Furthermore, SCS systems may have as many as thirty-two electrodes, which exponentially increases the number of modulation parameter value combinations available for programming. To facilitate such programming, a clinician often initially programs and modifies the modulation parameters through a computerized programming system, to allow the modulation parameters to be established from starting parameter sets (programs) and patient and clinician feedback. However, as the application of stimulation is applied to a patient over a period of time, the patient may desire a modification to the feeling, location, or type of neurostimulation treatment (such as to reduce variations to observed pain, to increase the amount of paresthesia coverage, or to modify the location of treatment). Thus, patient satisfaction with a particular stimulation output may change over time, and the initial settings and programming of the neurostimulator may not provide satisfactory therapy efficacy for the patient. The implementation and use of a patient feedback user interface and programming logic as described further in FIG. 6 and thereafter provides a mechanism for patient-initiated adjustment and modifications to implemented parameter settings, in a fashion that emphasizes therapy efficacy and perceived improvements of output provided from the neurostimulator deployment.

Figure 3:
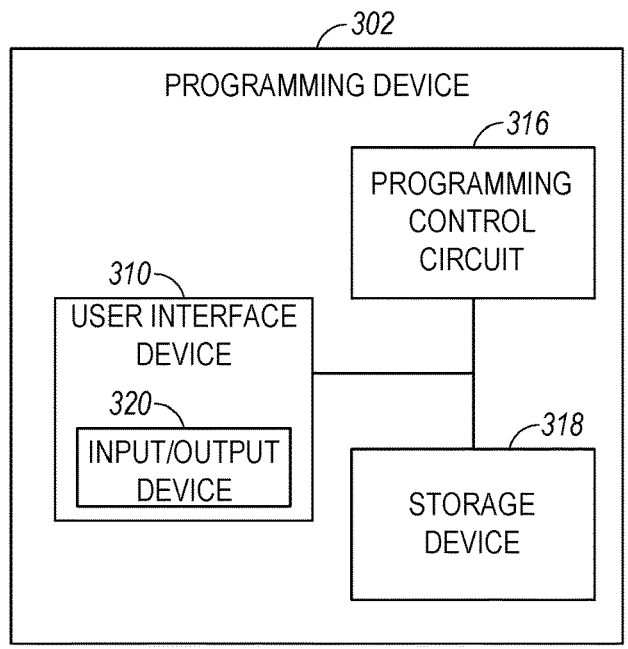
FIG. 3 illustrates, by way of example, an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface device 310. Programming control circuit 316 generates the plurality of stimulation parameters that controls the delivery of the neurostimulation pulses according to the pattern of the neurostimulation pulses. The user interface device 310 represents an embodiment to implement the user interface 110.

In various embodiments, the user interface device 310 includes an input/output device 320 that is capable to receive user interaction and commands to load, modify, and implement neurostimulation programs and schedule delivery of the neurostimulation programs. In various embodiments, the input/output device 320 allows the user to create, establish, access, and implement respective parameter values of a neurostimulation program through graphical selection (e.g., in a graphical user interface output with the input/output device 320), including values of a therapeutic neurostimulation field. In some examples, the user interface device 310 can receive user input to initiate the implementation of the programs which are recommended, modified, or loadable through various patient feedback user interfaces, which are described in more detail below.

In various embodiments, the input/output device 320 allows the patient user to apply, change, or modify certain building blocks of a program and a frequency at which the program is delivered. In various embodiments, the input/output device 320 can allow the patient user to save, retrieve, and modify programs (and program settings) loaded from a clinical encounter, managed from the patient feedback computing device, or stored in storage device 318 as templates. In various embodiments, the input/output device 320 and accompanying software on the user interface device 310 allows newly created building blocks, program components, programs, and program modifications to be saved, stored, or otherwise persisted in storage device 318.

In one embodiment, the input/output device 320 includes a touchscreen. In various embodiments, the input/output device 320 includes any type of presentation device, such as interactive or non-interactive screens, and any type of user input device that allows the user to interact with a user interface to implement, remove, or schedule the programs, and as applicable, to edit or modify waveforms, building blocks, and program components. Thus, the input/output device 320 may include one or more of a touchscreen, keyboard, keypad, touchpad, trackball, joystick, and mouse. In various embodiments, circuits of the neurostimulation system 100, including its various embodiments discussed in this document, may be implemented using a combination of hardware and software. For example, the logic of the user interface 110, the stimulation control circuit 214, and the programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
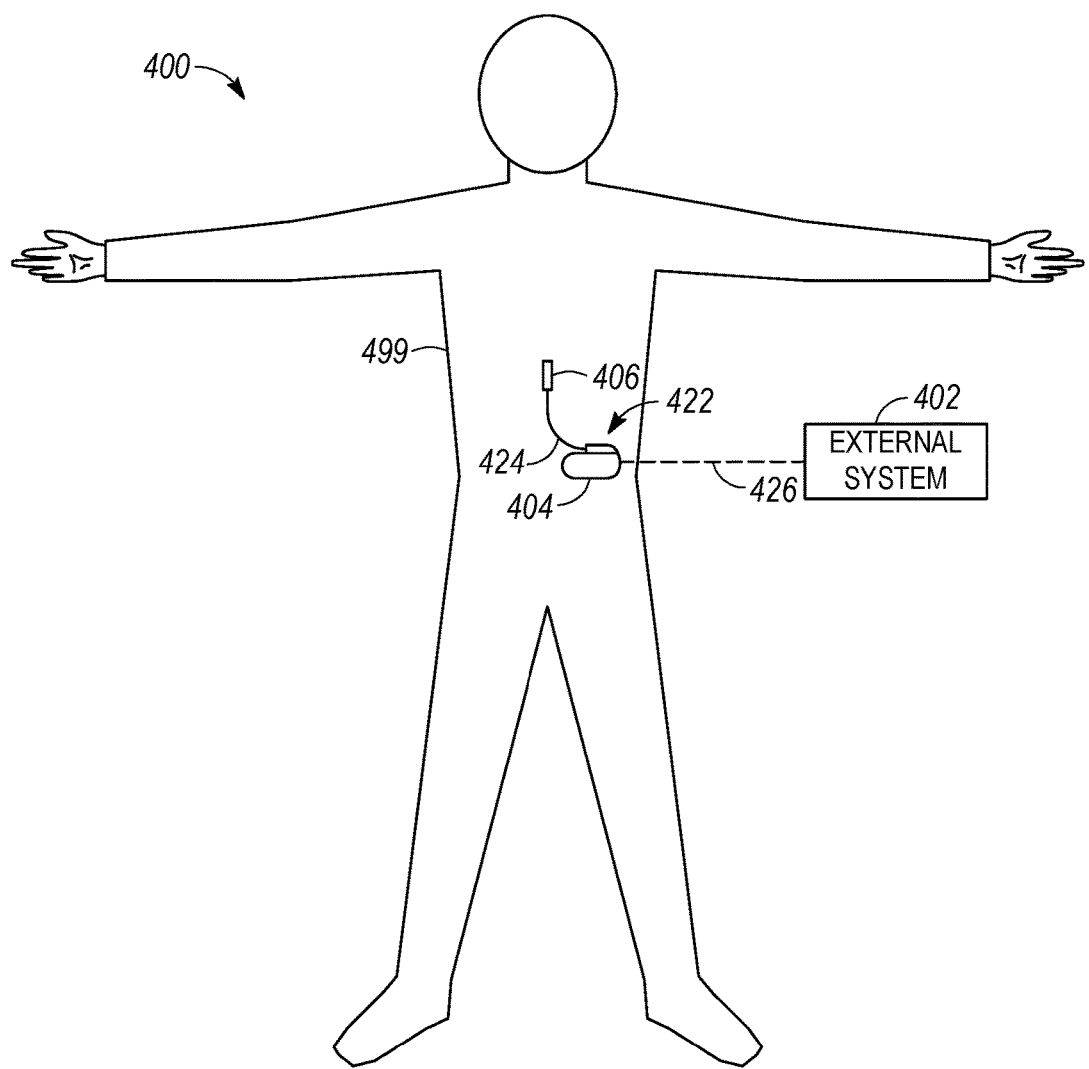
FIG. 4 illustrates, by way of example, an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between an implantable system 422 and an external system 402. Implantable system 422 is illustrated in FIG. 4 as being implanted in the patient's body 499. The system is illustrated for implantation near the spinal cord. However, the neuromodulation system may be configured to modulate other neural targets.

Implantable system 422 includes an implantable stimulator 404 (also referred to as an implantable pulse generator, or IPG), a lead system 424, and electrodes 406, which represent an embodiment of the stimulation device 204, the lead system 208, and the electrodes 206, respectively. The external system 402 represents an embodiment of the programming device 302.

In various embodiments, the external system 402 includes one or more external (non-implantable) devices each allowing the user and/or the patient to communicate with the implantable system 422. In some embodiments, the external system 402 includes a programming device intended for the user to initialize and adjust settings for the implantable stimulator 404 and a remote control device intended for use by the patient. For example, the remote control device may allow the patient to turn the implantable stimulator 404 on and off and/or adjust certain patient-programmable parameters of the plurality of stimulation parameters. The remote control device may also provide a mechanism to receive and process feedback on the operation of the implantable neuromodulation system. Feedback may include metrics or an efficacy indication reflecting perceived pain, effectiveness of therapies, or other aspects of patient comfort or condition. Such feedback may be automatically detected from a patient's physiological state, or manually obtained from user input entered in a user interface. As discussed in the following sections, a patient feedback computing device (which may be separate or integrated with the remote control device) may be used to process this feedback and implement modification to the program or program settings of the neuromodulation treatment in response to the feedback.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of tissue. It will be understood that other clinical effects and physiological mechanisms may also be provided through use of such stimulation techniques.

Figure 5:
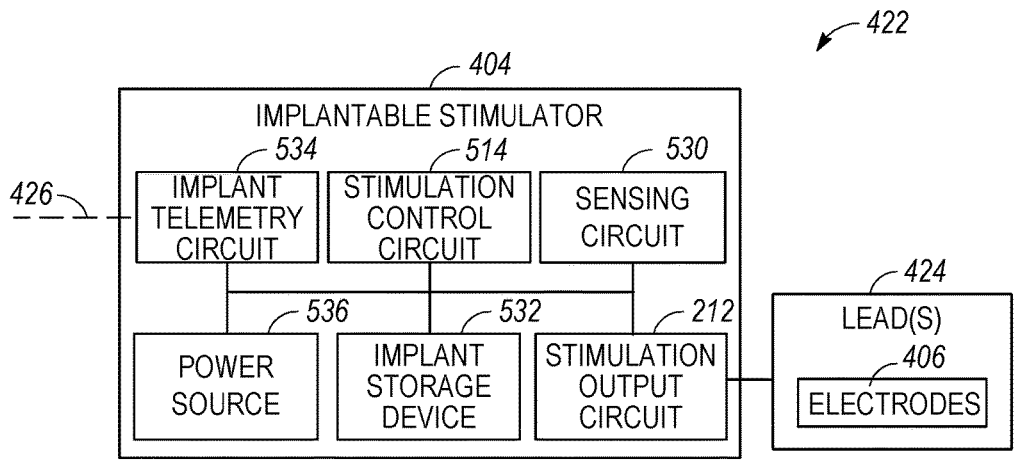
FIG. 5 illustrates, by way of example, an embodiment of an implantable stimulator and one or more leads of a neurostimulation system, such as the implantable neurostimulation system of FIG. 4.

FIG. 5 illustrates an embodiment of the implantable stimulator 404 and the one or more leads 424 of an implantable neurostimulation system, such as the implantable system 422. The implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. The sensing circuit 530, when included and needed, senses one or more physiological signals for purposes of patient monitoring and/or feedback control of the neurostimulation. Examples of the one or more physiological signals includes neural and other signals each indicative of a condition of the patient that is treated by the neurostimulation and/or a response of the patient to the delivery of the neurostimulation.

The stimulation output circuit 212 is electrically connected to electrodes 406 through the one or more leads 424, and delivers each of the neurostimulation pulses through a set of electrodes selected from the electrodes 406. The stimulation output circuit 212 can implement, for example, the generating and delivery of a customized neurostimulation waveform (e.g., implemented from a parameter of a program modified in response to a therapy efficacy indication input in a patient feedback user interface) to an anatomical target of a patient.

The stimulation control circuit 514 represents an embodiment of the stimulation control circuit 214 and controls the delivery of the neurostimulation pulses using the plurality of stimulation parameters specifying the pattern of the neurostimulation pulses. In one embodiment, the stimulation control circuit 514 controls the delivery of the neurostimulation pulses using the one or more sensed physiological signals and processed input from patient feedback interfaces. The implant telemetry circuit 534 provides the implantable stimulator 404 with wireless communication with another device such as a device of the external system 402, including receiving values of the plurality of stimulation parameters from the external system 402. The implant storage device 532 stores values of the plurality of stimulation parameters, including parameters from one or more programs obtained using the patient feedback and the programming modification logic techniques disclosed herein.

The power source 536 provides the implantable stimulator 404 with energy for its operation. In one embodiment, the power source 536 includes a battery. In one embodiment, the power source 536 includes a rechargeable battery and a battery charging circuit for charging the rechargeable battery. The implant telemetry circuit 534 may also function as a power receiver that receives power transmitted from external system 402 through an inductive couple.

In various embodiments, the sensing circuit 530 (if included), the stimulation output circuit 212, the stimulation control circuit 514, the implant telemetry circuit 534, the implant storage device 532, and the power source 536 are encapsulated in a hermetically sealed implantable housing. In various embodiments, the lead(s) 424 are implanted such that the electrodes 406 are placed on and/or around one or more targets to which the neurostimulation pulses are to be delivered, while the implantable stimulator 404 is subcutaneously implanted and connected to the lead(s) 424 at the time of implantation.

FIG. 6 illustrates an embodiment of an external patient programming device 602 of an implantable neurostimulation system, such as the external system 402, with the external patient programming device 602 illustrated to receive commands from a patient feedback computing device 670. The external patient programming device 602 represents an embodiment of the programming device 302, and includes an external telemetry circuit 640, an external storage device 618, a programming control circuit 616, a user interface device 610, a controller 650, and an external communication device 620.

The external telemetry circuit 640 provides the external patient programming device 602 with wireless communication to and from another controllable device such as the implantable stimulator 404 via the telemetry link 426, including transmitting one or a plurality of stimulation parameters (including changed stimulation parameters) to the implantable stimulator 404. In one embodiment, the external telemetry circuit 640 also transmits power to the implantable stimulator 404 through inductive coupling.

The external communication device 620 provides a mechanism to conduct communications with the patient feedback computing device 670 via an external communication link 680 to a communication device 682. As described in the following disclosure, the patient feedback computing device 670 may provide data to the external patient programming device 602 that corresponds to a modification of a setting for a neurostimulation program or characteristics of a neurostimulation program (which is, in turn, determined from a therapy efficacy indication selected in a graphical user interface). The patient feedback computing device 670 may also receive data from the external patient programming device 602 that indicates current or previous characteristics of programming or treatment, including medical characteristics unique to the patient, a status of the neurostimulation device, and the like. The external communication device 620 and the patient feedback computing device 670 may communicate using any number of wired or wireless communication mechanisms described in this document, including but not limited to an IEEE 802.11 (Wi-Fi), Bluetooth, Infrared, and like standardized and proprietary wireless communications implementations. Although the external telemetry circuit 640 and the external communication device 620 are depicted as separate components within the external patient programming device 602, the functionality of both of these components may be integrated into a single communication chipset, circuitry, or device.

The external storage device 618 stores a plurality of existing neurostimulation waveforms, including definable waveforms for use as a portion of the pattern of the neurostimulation pulses, settings and setting values, other portions of a program, and related treatment efficacy indication values. In various embodiments, each waveform of the plurality of individually definable waveforms includes one or more pulses of the neurostimulation pulses, and may include one or more other waveforms of the plurality of individually definable waveforms. Examples of such waveforms include pulses, pulse blocks, pulse trains, and train groupings, and programs. The existing waveforms stored in the external storage device 618 can be definable at least in part by one or more parameters including, but not limited to the following: amplitude, pulse width, frequency, duration(s), electrode configurations, total charge injected per unit time, cycling (e.g., on/off time), waveform shapes, spatial locations of waveform shapes, pulse shapes, number of phases, phase order, interphase time, charge balance, and ramping.

The external storage device 618 also stores a plurality of individually definable fields that may be implemented as part of a program. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes. A variety of settings in a program (including settings changed as a result of patient therapy efficacy feedback) may be correlated to the control of these waveforms and definable fields.

The programming control circuit 616 represents an embodiment of a programming control circuit 316 and generates the plurality of stimulation parameters, which is to be transmitted to the implantable stimulator 404, based on the pattern of the neurostimulation pulses. The pattern is defined using one or more waveforms selected from the plurality of individually definable waveforms (e.g., defined by a program) stored in an external storage device 618. In various embodiments, a programming control circuit 616 checks values of the plurality of stimulation parameters against safety rules to limit these values within constraints of the safety rules. In one embodiment, the safety rules are heuristic rules.

The user interface device 610 represents an embodiment of the user interface device 310 and allows the user (including a patient or clinician) to select, modify, enable, disable, activate, schedule, or otherwise define a program or sets of programs for use with the neurostimulation device and perform various other monitoring and programming tasks for operation of the neurostimulation device. The user interface device 610 can enable a user to implement, save, persist, or update a program including the program or program parameters recommended or indicated by the patient feedback computing device 670. The user interface device 610 includes a display screen 642, a user input device 644, and an interface control circuit 646. The display screen 642 may include any type of interactive or non-interactive screens, and the user input device 644 may include any type of user input devices that supports the various functions discussed in this document, such as a touchscreen, keyboard, keypad, touchpad, trackball, joystick, and mouse. In one embodiment, the user interface device 610 includes an interactive screen that displays a graphical representation of one or more stimulation waveforms associated with a program or program parameters recommended or indicated by the patient feedback computing device 670. In a further embodiment, the user interface device 610 allows a clinician user to access or adjust advanced settings of the neurostimulation device, such as modification of the waveform (or other aspects of the program or program parameters) by graphically editing the waveform and/or various building blocks of the waveform, or by modifying other aspects of the program or program parameters. The user interface device 610 may also allow the user to perform any other functions discussed in this document where user interface input is suitable. Thus, in some examples, the features of patient feedback computing device 670 may be integrated into the user interface device 610.

Interface control circuit 646 controls the operation of the user interface device 610 including responding to various inputs received by the user input device 644 that define or modify characteristics of implementation (including conditions, schedules, and variations) of one or more programs, parameters within the program, characteristics of one or more stimulation waveforms within a program, and like neurostimulator operational values that may be entered or selected with the external patient programming device 602, or obtained from the patient feedback computing device 670. Interface control circuit 646 includes a neurostimulation program circuit 660 that may generate a visualization of such characteristics of implementation, and receive and implement commands to implement the program and the neurostimulator operational values (including a status of implementation for such operational values). These commands and visualization may be performed in a review and guidance mode, or in a real-time programming mode. For example, in a real-time programming mode, the programming control circuit 616 dynamically updates values of the plurality of stimulation parameters in response to user input such as selection of a therapy efficacy indication received from the patient feedback computing device 670, and the programming control circuit 616 accordingly transmits the plurality of stimulation parameters with the updated values defined by the selected modified program to the implantable stimulator 404.

The controller 650 can be a microprocessor that communicates with the external telemetry circuit 640, the external communication device 620, the external storage device 618, the programming control circuit 616, and the user interface device 610, via a bidirectional data bus. The controller 650 can be implemented by other types of logic circuitry (e.g., discrete components or programmable logic arrays) using a state machine type of design. As used in this disclosure, the term "circuitry" should be taken to refer to either discrete logic circuitry, firmware, or to the programming of a microprocessor.

In accordance with various techniques of this disclosure, the controller 650 can receive, via the user interface device 610 for example, user input that at least partially defines implementation characteristics of a neurostimulation program (e.g., initial therapy settings) to provide therapy to a patient A change to a setting or parameter of the neurostimulation program (or a selection of another neurostimulation program) may be received or obtained from operation of the programming logic 678 operating in the patient feedback computing device 670. For example, the programming logic 678 may operate an algorithm or logic function to determine an appropriate modification to a program based on user input received by the patient feedback computing device 670 in a user interface 672. In response to the receipt of the modification or an indication of the modification from the patient feedback computing device 670, the controller 650 can execute instructions that cause the programming control circuit 616 to generate a plurality of stimulation parameters for the neurostimulation field in accordance with a selected or modified neurostimulation program (and any changes to the settings of the neurostimulation program from operation of the programming logic 678). For instance, the programming control circuit 316 can activate a different subset of electrodes from the number of available electrodes on the lead(s), modify a virtual location of treatment from the electrodes, or modify the current distributions associated with electrodes in the subset (including various pulses and waveforms modified in the neurostimulation program).

Using the external patient programming device 602 and the patient feedback computing device 670, user interface devices 610 or 672 can capture therapy efficacy from a patient regarding perceived characteristics of a therapy program, which can then be processed to identify one or more modifications to the therapy program. For example, the patient feedback computing device 670 may be used to receive patient input in the user interface 672 using an input device 676 (e.g., touchscreen input) that receives an indication of a current treatment state; the patient feedback computing device 670 may also be used to generate patient output in the user interface 672 using an output device 674 (e.g., display screen) to provide an indication of the current treatment state. Other forms of input and output devices (e.g., keyboard, keypad, touchpad, trackball, joystick, mouse, microphone, speaker, camera, human interface sensor) may be used. In response to the input and output of a therapy efficacy indication with the user interface 672, the programming logic 678 can identify a modification to the program and determine an updated stetting for at least one of the plurality of programmable parameter settings.

The patient feedback computing device 670 may provide a mechanism to transfer settings of the recommended program or program data to the external patient programming device 602, such as with use of the communication device 682 and the external communication link 680. The external patient programming device 602 can receive additional modification(s) to the program, e.g., using the user interface device 610, such as by allowing a user to select and adjust specific parameter settings of the program (or start/stop/schedule the program). As also discussed in the following examples, using the patient feedback computing device 670, a series of user interface inputs may be received and processed to identify the therapy efficacy and correlate the therapy efficacy to some program setting modification in real-time.

As will be understood, the variety of settings for a neurostimulation device may be provided by many variations of programming parameter settings. Existing patient programmers provide the ability for a patient to cycle through programs that have a wide variety of programming parameters, with hundreds or thousands of specific settings being rolled up into a single program. An inordinately large number of such program parameter combinations exist, and often a clinician determines a specific set of parameter combinations (and programs) to deploy to a patient simply based on expertise and trial and error. The following system and methods provide applied mechanisms adjust parameter settings to certain therapies in response to real-time, captured feedback of the treatment type, treatment locations, symptoms, and clinical objectives of therapy efficacy directly from the patient. These adjustments may be implemented as a modification to one or more settings in a program, new programs, a macro-based or automated implementation of a subset of settings in a program, recommended or suggested adjustments or modifications to an existing program, and like variations.

In an example, the patient feedback computing device 670 may be provided in the form factor of a software application (e.g., "mobile app") natively operating or executing on a mobile device such as a smartphone or tablet (e.g., a software application that is installed, programmed, or customized to the hardware characteristics of a subject computing device.) Thus, the functionality of the patient feedback computing device 670 may be provided by an external device separate from the external patient programming device 602. In another example, the features of the patient feedback computing device 670 may be provided from an integrated device hosting the external patient programming device 602 and the patient feedback computing device 670, e.g., an apparatus that integrates programming and therapy efficacy feedback functions into a single patient-operated unit.

Figure 7:
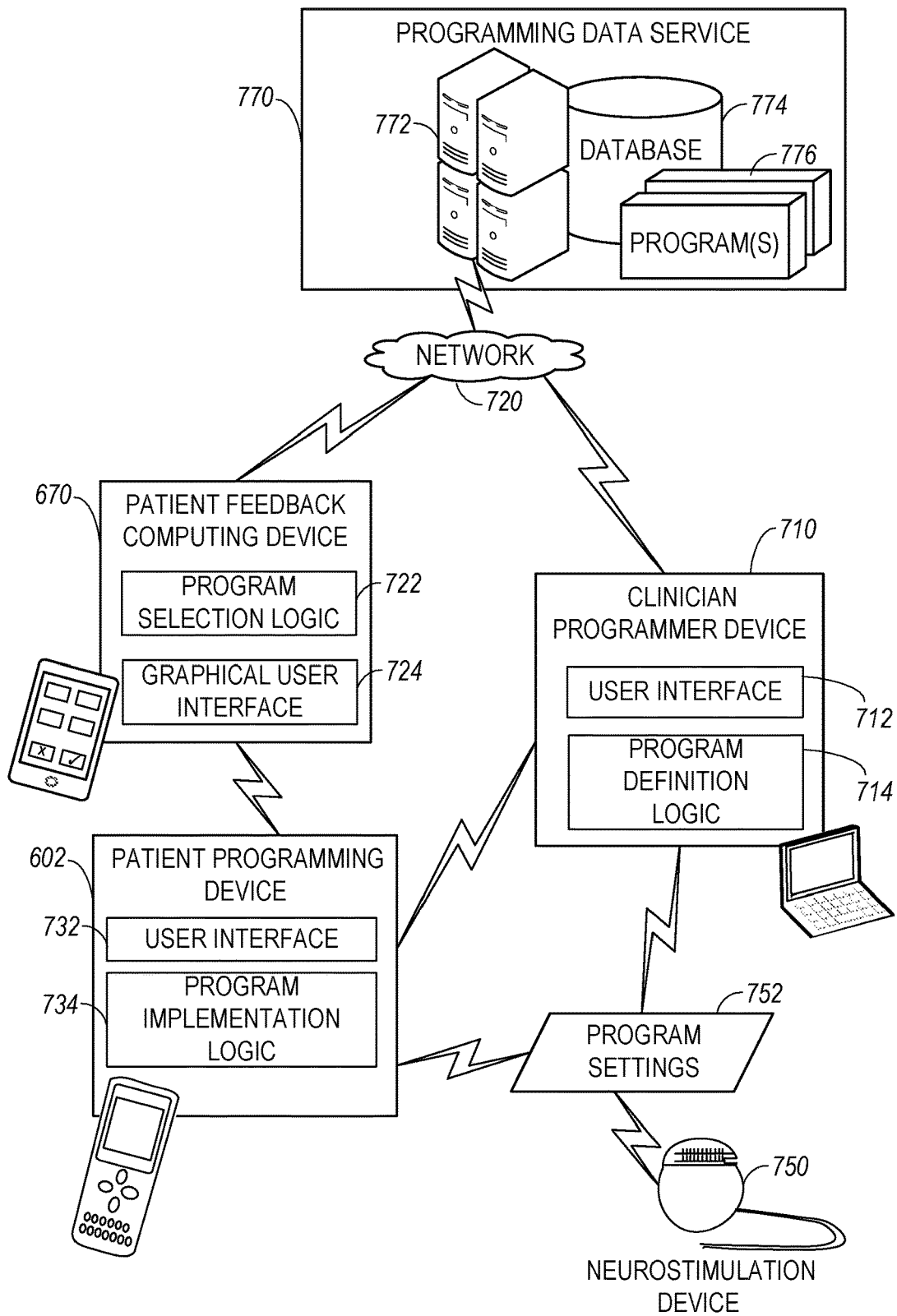
FIG. 7 illustrates, by way of example, an embodiment of data interactions among a clinician programmer device, a patient feedback computing device, a patient programming device, and a programming data service for providing and modifying respective programs of defined parameter settings for operation of a neurostimulation device.

FIG. 7 illustrates, by way of example, an embodiment of data interactions among a clinician programmer device 710, a patient feedback computing device 670, an external patient programming device 602, and a programming data service 770 for providing and modifying respective programs of defined parameter settings for operation of a neurostimulation device. The patient feedback computing device 670 is shown in FIG. 7 in the form of a touchscreen computing device (e.g., a smartphone or tablet) with the touchscreen computing device being specially programmed to provide a graphical user interface 724 (e.g., in a software app interface) and operate program selection logic 722 (e.g., with an algorithm implemented in software that is executed on the computing device). It will be understood that other form factors and embodiments of the patient feedback computing device 670, including the integration of the other programming devices or specialized circuitry, may also be deployed.

The patient feedback computing device 670 and the clinician programmer device 710 may communicate to a programming data service 770 via a network 720 (e.g., a private local area network, public wide area network, the Internet, and the like) to obtain programs, program settings, program modifications, recommendations, or like information related to programming or treatment efficacy. The programming data service 770 serves as a data service to host program information for a plurality of neurostimulation programs (e.g., across multiple patients, facilities, or facility locations). In an example, the programming data service 770 may be operated or hosted by a research institution or a medical device provider (e.g., a manufacturer of the neurostimulation device) for managing data and settings for respective programs 776 among a plurality of clinical deployments. The programming data service 770 may provide an interface to backend data components such as a data processing server 772 and a database 774, to provide a plurality of programs 776 and program settings. The database 774 of programming settings may include patient- or clinician-specific programs and settings (including settings used by clinicians in initial programming or re-programming of the device). The programming data service 770 may be accessed using an application programming interface (API) or other remotely accessible interface accessible via the network 720.

The graphical user interface 724 of the patient feedback computing device 670 is configured to receive and collect patient feedback in the form of therapy efficacy indications, and output an indication of modifications in response to the patient feedback. The program selection logic 722 is configured to identify, based on one or more of the therapy efficacy indications input and selected in the user interface, updated program setting(s) 752 for the corresponding programming parameter(s) and program(s) of the neurostimulation device 750.

In an example, the program settings 752 to update the parameter(s) or program(s) of the neurostimulation device 750 are first communicated from the patient feedback computing device 670 to the external patient programming device 602, with the program settings 752 then being communicated to the neurostimulation device 750 by the external patient programming device 602. In another example, the program selection logic 722 results in selection (and potentially, creation) of an entirely new program, which may be communicated in the program settings 752. The clinician programmer device 710 can operate in a similar fashion, with use of a user interface 712 and program definition logic 714 to select, define, edit, and modify parameter(s) or program(s) in a clinical setting (and may be directly communicated with the program settings 752).

The external patient programming device 602 is illustrated in the form factor of a patient-operable remote control. The external patient programming device 602 operates to communicate program data to the neurostimulation device 750 through use of program implementation logic 734 and a user interface 732 (e.g., a user interface provided by the user interface device 610 discussed in FIG. 6). In an example, a therapy efficacy indication is transmitted to the external patient programming device 602 from the patient feedback computing device 670, and is processed by the program implementation logic 734 to determine an appropriate parameter change to an existing program. In another example, a therapy efficacy indication is entered directly in the user interface of the external patient programming device 602, and the program implementation logic 734 is used to create and determine parameters of a new program.

Figure 8:
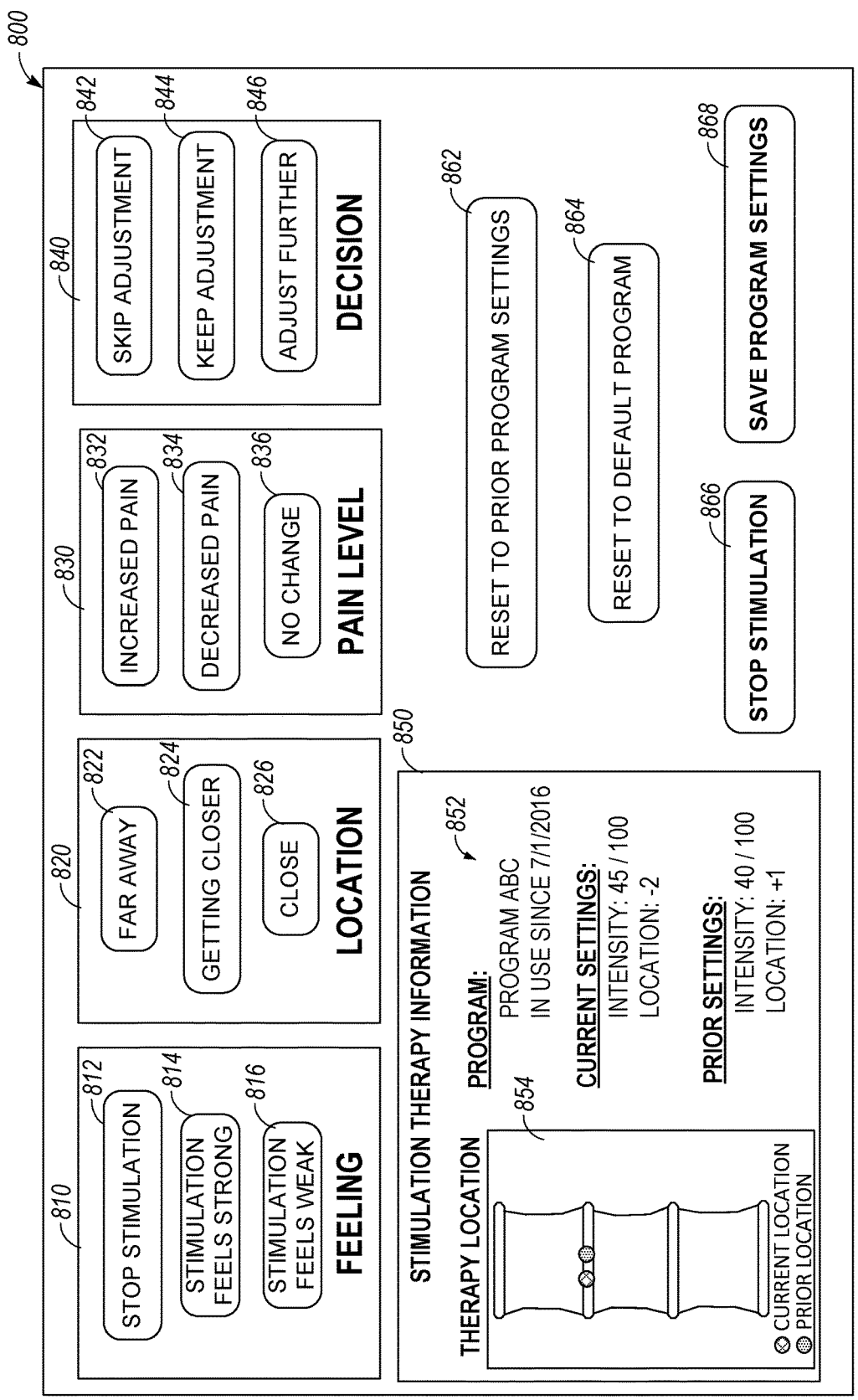
FIG. 8 illustrates, by way of example, an embodiment of a graphical user interface of a patient-operated computing device for selecting and receiving user input corresponding to a therapy efficacy indication of a neurostimulation treatment.

FIG. 8 illustrates, by way of example, an embodiment of a graphical user interface 800 of a patient-operated computing device for selecting and receiving user input corresponding to a therapy efficacy indication of a neurostimulation treatment. For example, the graphical user interface 800 may embody the characteristics of the graphical user interface 724 of the patient feedback computing device 670, or other features of the respective user interfaces (including user interfaces 712, 732).

The graphical user interface 800 includes one or more inputs to receive respective forms of therapy efficacy indications for a program being initiated or operated in a neurostimulator device deployment. The graphical user interface 800 may be operated by a patient for direct receipt of therapy efficacy values and therapy responses, although it will be understood that various features and information of the graphical user interface 800 may be disabled, enabled, hid, or supplemented based on the type of user of the graphical user interface 800 and the permissions established for the user (such as a physician, a technical service agent, or the like).

The graphical user interface 800 is depicted as including various selection fields to receive information regarding therapy efficacy characteristics of the treatment or treatment change, as perceived by the patient. For example, the therapy efficacy characteristics may include: inputs for feeling 810 to provide an indication of the perceived stimulation intensity of the neurostimulation treatment, such as the stimulation feels strong (input 814), the stimulation feels weak (input 816), or the stimulation needs to be stopped (input 812); inputs for location 820 to provide an indication of the perceived location of the neurostimulation treatment, such as the treatment is perceived as far away from a desired location (input 822), getting closer to a desired location (input 824), or is close/located in proximity or at a desired location (input 824); inputs for pain level 830 to provide an indication of the perceived pain level resulting after the neurostimulation treatment, such as the treatment is perceived as resulting in increased pain (input 832), decreased pain (input 834), or no change in pain level (input 836). The selection fields may also include decision inputs 840 to skip (or undo, revert, or reverse) the adjustment (input 842), keep or save the adjustment (input 844), or make further adjustment (input 846). Other inputs not shown in the graphical user interface 800 may provide a more detailed input of therapy efficacy related to the nature of pain, location of pain, intensity of pain, spread of pain, comfort measurements, sensations, stimulation effect(s), stimulation location(s) (including stimulation in an undesirable area such as ribs), or other physiological characteristics of the medical condition or medical condition treatment.

In addition to (or in substitute of) receiving indications of changes to pain, the inputs in the graphical user interface 800 may be used for receiving indications of changes to stimulation level, comfort level, or treatment efficacy. Various levels or measurements of indicated results may correspond to threshold levels for perception, comfort, or discomfort to control or calibrate changes applied by a selection algorithm. For example, a calibration table may be created, updated, or implemented in response to certain responses or actions in the graphical user interface 800 exceeding a predefined or detected level.

The inputs of the graphical user interface 800 may be received using any number of user interface controls, such as buttons, input boxes, drop-downs, graphical selection screens, and the like. In some examples, updated program settings may be immediately communicated to the neurostimulation device (in real-time) in response to user input of the inputs 810, 820, 830, 840 in the user interface; in other examples, combinations of multiple user inputs must be selected or indicated (such as a combination of user input from feeling, location, pain level, and decision) before updated program settings are communicated to the neurostimulation device.

The graphical user interface 800 can include outputs for information corresponding to a selectable program. For example, a listing of stimulation therapy information 850 may include information 852 on a current program being used or selected from a library of programs (such as the name, data, usage characteristics of the program), and settings modified or changed for the program (such as settings related to intensity, feeling, or location). The listing of stimulation therapy information 850 may also include a graphical representation 854 of a location of therapy, such as an indication of how the center point of stimulation has been moved from a first location to a second location in response to therapy efficacy indications of location (e.g., with inputs 822, 824, or 826). In further examples, the listing of stimulation therapy information 850 may include physiological data values that are automatically detected by the neurostimulation device or another device.

The graphical user interface 800 may provide selectable features to reverse, revert, or undo modifications. For example, the selectable features may include a selectable option to reset to one or more prior program settings (input 862), or reset to a default program (input 864) (e.g., an initial program). The graphical user interface 800 also may provide selectable features to stop stimulation (input 866), or to save program settings (input 868). Other mechanisms to access or modify other candidate programs (e.g., to implement a specific saved program, or to apply modifications across multiple programs) may be used. It will be understood that a variety of other inputs and outputs may be provided for user interaction in the graphical user interface 800 or other embodiments of the clinical guidance user interface.

Figure 9:
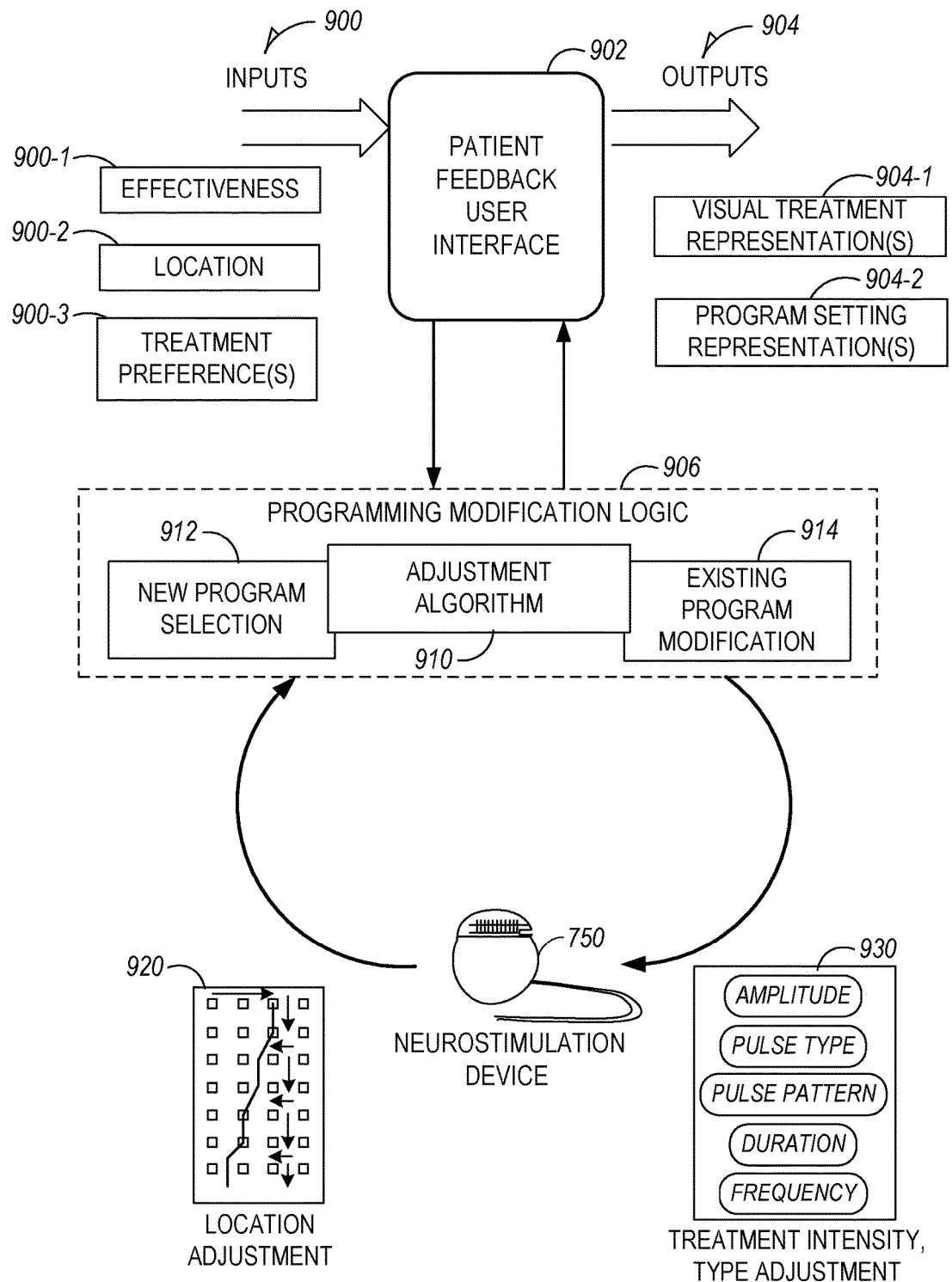
FIG. 9 illustrates, by way of example, an embodiment of a data and control flow between a user interface and programming modification logic used to communicate and modify programming parameters of a neurostimulation device.

FIG. 9 illustrates, by way of example, an embodiment of a data and control flow between a user interface and programming modification logic used to communicate and modify programming parameters of a neurostimulation device (e.g., the neurostimulation device 750). As illustrated, the data and control flow may include a plurality of inputs 900 that are provided to a patient feedback user interface 902, and a plurality of outputs 904 provided from the patient feedback user interface 902.

The inputs that can be provided to the patient feedback user interface 902 as part of a program modification process (e.g., in a user interface to modify the program based on input therapy efficacy indications) may include measurements and indications of: therapy effectiveness 900-1, relevant to the medical condition of the patient, such as changes in pain level, pain area, spread of pain, or other pain characteristics; therapy location 900-2, relevant to the spatial aspects of neurostimulation treatment applied to the patient, such as movement or closeness of the treatment in a pain or treatment area; and therapy treatment preferences 900-3, relative to the perceived or desired level of stimulation, such as intensity of stimulation, type of stimulation, timing of stimulation, and the like.

Based on the therapy efficacy indications that correspond to the inputs 900-1, 900-2, 900-3, the programming modification logic 906 operates an adjustment algorithm 910. The adjustment algorithm may identify a new program selection 912 or existing program modification 914 based on a degree or type of therapy efficacy indication and the characteristics of the therapy efficacy indication. The results of the new program selection 912 or the existing program modification 914 may be communicated to the neurostimulation device 750. For example, the settings changed on the neurostimulation device 750 may result in a location adjustment 920 to the location of the neurostimulation treatment, or a treatment intensity or type adjustment 930 to the amplitude, pulse type, pulse pattern, duration, frequency, or other characteristics of the neurostimulation energy output by the neurostimulation device 750.

The use of the patient feedback user interface 902 can assist patients with real-time feedback and modification to determine which parameters are most suitable or beneficial for use in the neurostimulation device (and, which indications of pain, location, and treatment are most important to a particular patient). This real-time feedback may be assisted through the plurality of outputs 904. For example, the patient feedback user interface 902 may output data via the patient feedback user interface 902, including the selection of visual treatment representations 904-1, program setting representations 904-2, and related indications or statuses. The use of the patient feedback user interface 902 can also assist patients with a determination or recommendation of which program parameters are most suitable or beneficial for modification or change in the neurostimulation device. Thus, although clinician-established programs may provide a starting point for treatment, further modification to the treatment through the modification techniques discussed herein can assist variation attributable to the patient's preferences or unique condition.

The patient feedback user interface 902 may provide other functions to allow the persistence (e.g., saving or backup) of a new or modified program, which may be communicated to the programming device, external systems, or other locations. The new or modified program, modification settings, and therapy efficacy indications may also be logged for diagnostic and evaluation purposes. For example, the type of therapy efficacy indications that are entered among multiple users may indicate a preferred treatment approach or efficacy (or lack of efficacy) of a particular program or setting.

Figure 10:
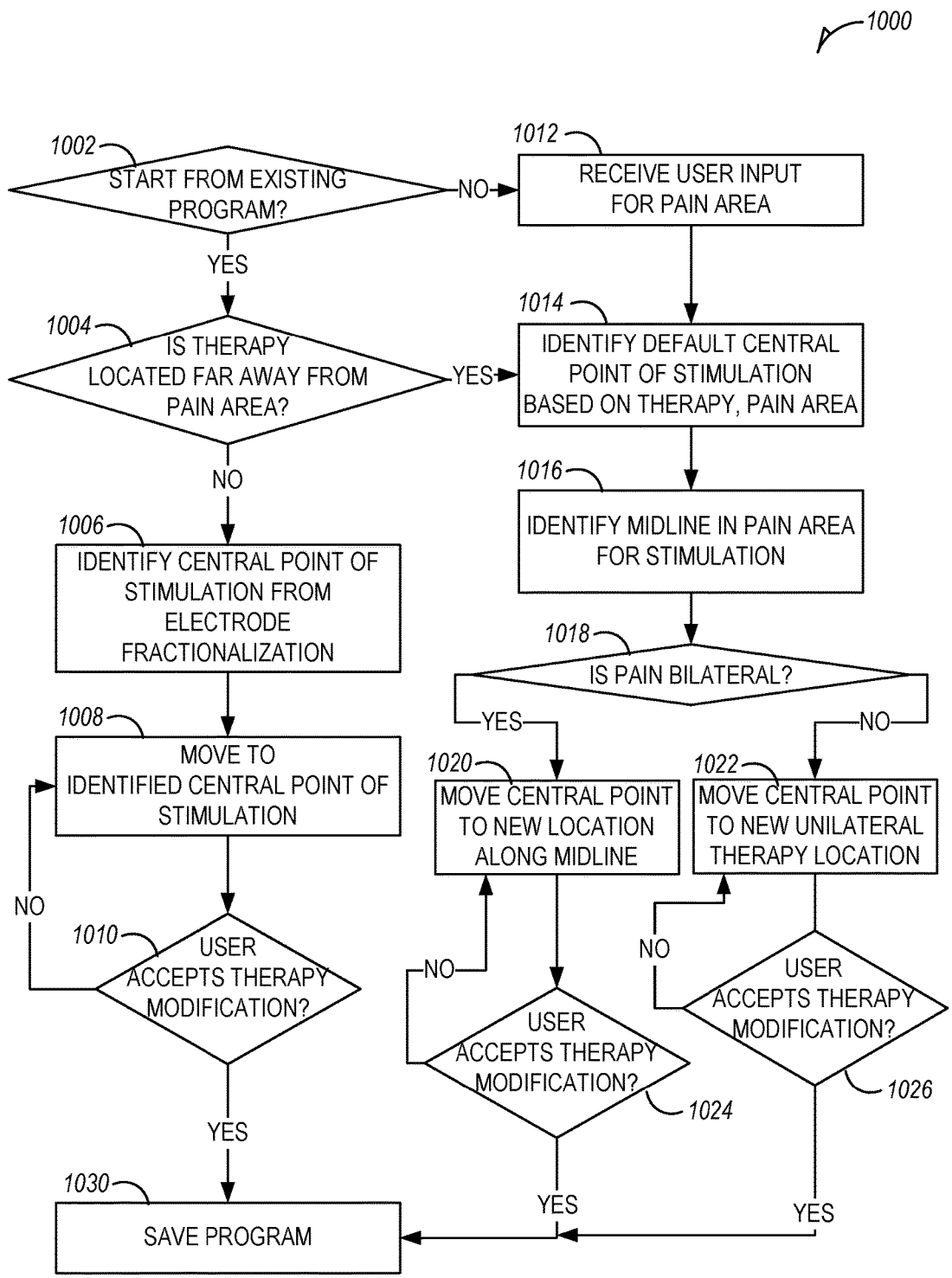
FIG. 10 illustrates, by way of example, an embodiment of a method implemented by programming modification logic for accessing and modifying a program of parameters for a neurostimulation device.

FIG. 10 illustrates, by way of example, an embodiment of a method 1000 implemented by a programming modification logic for accessing and providing a program of parameters for a neurostimulation device. This method 1000 may be implemented with use of electronic operations within a patient feedback computing device, such as the operations invoked by user interfaces (e.g., 724, 800, and 902) discussed above.

For example, the programming modification logic operates to provide an evaluation based on the use of an existing program (decision 1002). If the evaluation is performed upon the use of an existing program, then further evaluation is performed to determine whether the therapy is indicated by the patient as occurring far away from the pain area (decision 1004). If the evaluation is being performed on a new program, then the programming modification logic operates to receive user input for the pain area (operation 1012), and identify a new (e.g., default) central point of stimulation based on the type of therapy and the pain area (operation 1014). If the therapy is located far away from the pain area (as indicated by decision 1004), this will also identify a new central point of stimulation based on the type of therapy and the pain area (operation 1014).

Continuing with the case where the therapy is located proximate (e.g., not far away) from the pain area (e.g., as indicated by decision 1004), the programming modification logic operates to identify and establish a central point of stimulation with use of electrode fractionalization (operation 1006). Specifically, electrode fractionalization techniques can be used to create, move, shape, or shift the central point of stimulation. The location of therapy is then modified to move the therapy to the new identified central point of stimulation (operation 1008), and appropriate setting values are updated with the neurostimulation device. If the user accepts the therapy modification in the new location (decision 1010), the program is saved and persisted for use with the neurostimulation device (operation 1030). If the user does not accept the therapy modification in the new modification (as a result of decision 1010), then the location of the therapy is further modified to move the therapy to another identified central point of stimulation (operation 1008), and appropriate setting values are updated with the neurostimulation device. This may continue until a satisfactory location is indicated and the program is saved, or the location and program modification is rejected entirely.

Continuing with the case where the therapy is not located proximate (e.g., not far away) from the pain area (e.g., as indicated by decision 1004), and a new default central point of stimulation is determined from the therapy and pain area (operation 1014), the programming modification logic operates to identify a central point of stimulation with use of a midline in a known pain area (operation 1016). If the pain is identified as being bilateral (in decision 1018, e.g., as perceived and identified by the patient), then the central point of stimulation is moved to a new location along the identified midline (operation 1020). If the pain is identified as not being bilateral (in decision 1018, e.g., as perceived and identified by the patient), then the central point of stimulation is moved to a new unilateral therapy location (operation 1022). After moving to a new location along the midline (operation 1020) or a new unilateral therapy location (operation 1022), if the user accepts the therapy modification in the new location (decisions 1024, 1026), the program is saved and persisted for use with the neurostimulation device (operation 1030). If the user does not accept the therapy modification in the new modification (as a result of decisions 1024, 1026), then the location of the therapy is further modified to move the therapy to another identified central point of stimulation (operations 1020, 1022), and appropriate setting values are updated with the neurostimulation device. Again, this may repeat until a satisfactory location is indicated and the program is saved, or the location and program modification is rejected entirely.

Figure 11:
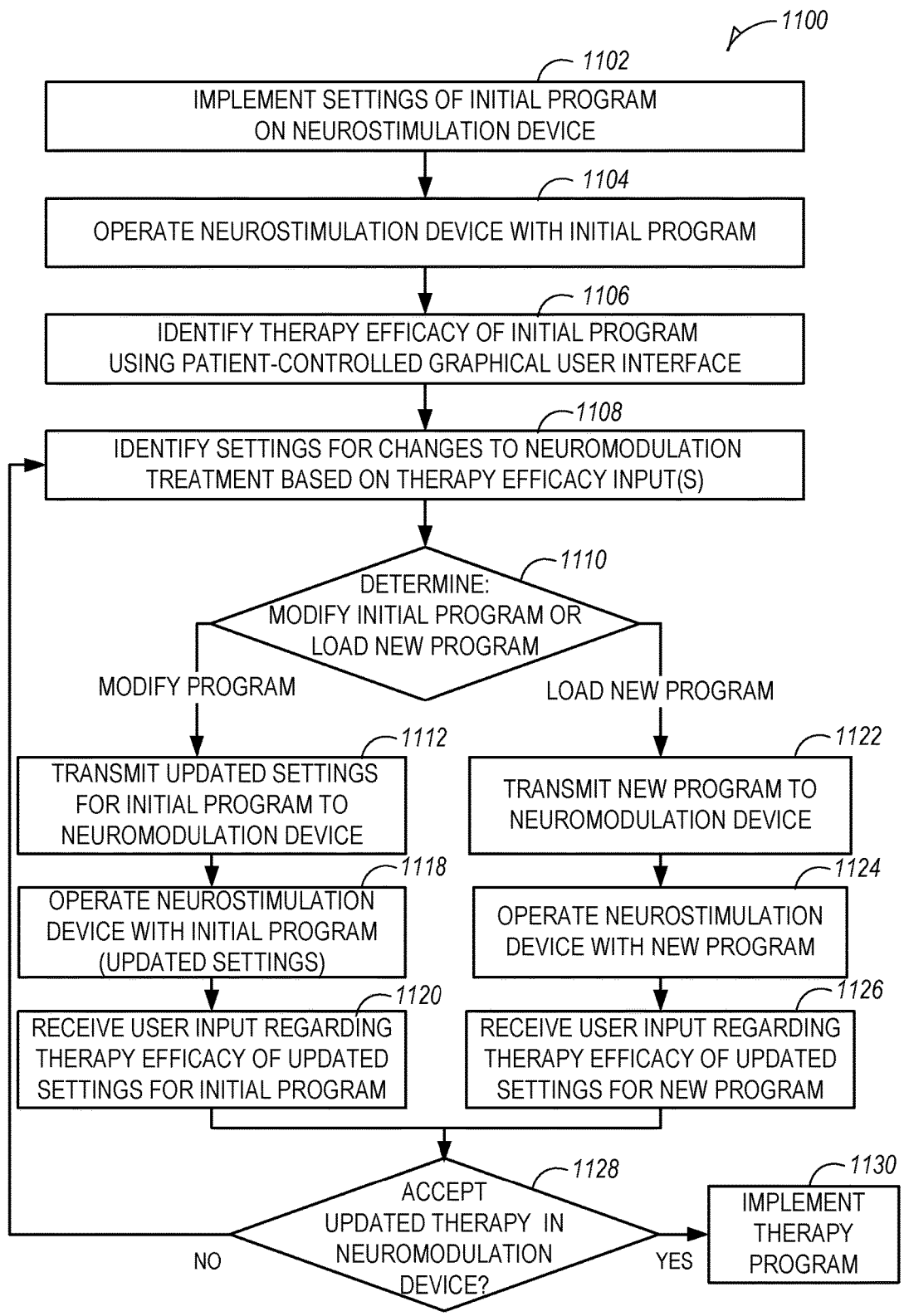
FIG. 11 illustrates, by way of example, an embodiment of a method implemented by a patient feedback computing device and a patient programming device for accessing and modifying a program of parameters for a neurostimulation device.

FIG. 11 illustrates, by way of example, an embodiment of a method 1100 implemented by a patient feedback computing device and a patient programming device for accessing and modifying a program of parameters for a neurostimulation device. This method 1100 may be implemented with use of electronic operations within a programming device, such as with the patient feedback computing device 670, patient programming device 602, and the user interfaces and logic of such devices discussed above.

For example, the patient programming device can operate to implement settings of a neurostimulation treatment based on an initial program, such as a program selected by a clinician or patient (operation 1102), and the neurostimulation device delivers treatment to the patient based on use of the initial program (operation 1104). The patient feedback computing device presents a user interface to receive user input of effectiveness of the initial program, to receive user input providing one or more indications of the therapy efficacy (operation 1006), with such user input relating to effectiveness, location, treatment preferences, and the like. Program modification logic operating at the patient feedback computing device or patient programming device operates to identify settings to change the neuromodulation treatment based on the therapy efficacy user input (operation 1106).

The program modification logic can further operate to determine whether to modify the initial program (e.g., change a setting of the initial program) or load a new program (e.g., implement other setting groups of another program) (decision 1110). This determination may be based on the type of therapy efficacy indicated, whether the treatment location is moved, and other factors (e.g., as suggested in method 1000).

If the initial program is modified, updated settings for the initial program are transmitted from the programming device to the neuromodulation device (operation 1112), and the neurostimulation device is operated with updated settings of the initial program (operation 1118). The user interface then receives additional user input regarding the therapy efficacy of the updated settings of the initial program (operation 1120).

If the initial program is not modified, a new program is transmitted from the programming device to the neuromodulation device (operation 1122), and the neurostimulation device is operated with updated settings of the new program (operation 1124). The user interface again can receive additional user input regarding the therapy efficacy of the updated settings of the new program (operation 1126).

Based on the user input or an indication from the patient, the program modification logic determines whether to accept the updated therapy settings or program in the neuromodulation device (decision 1128). If the updated therapy settings or program is accepted, the therapy program is persisted to the neurostimulation device and the therapy program is implemented in a routine or schedule of therapy operations (operation 1130). If the updated therapy settings or program is not accepted, then operations to identify additional settings for change and locate another setting, program, or reversal of the setting or program, are implemented (e.g., repeating operations 1112 to 1126).

Figure 12:
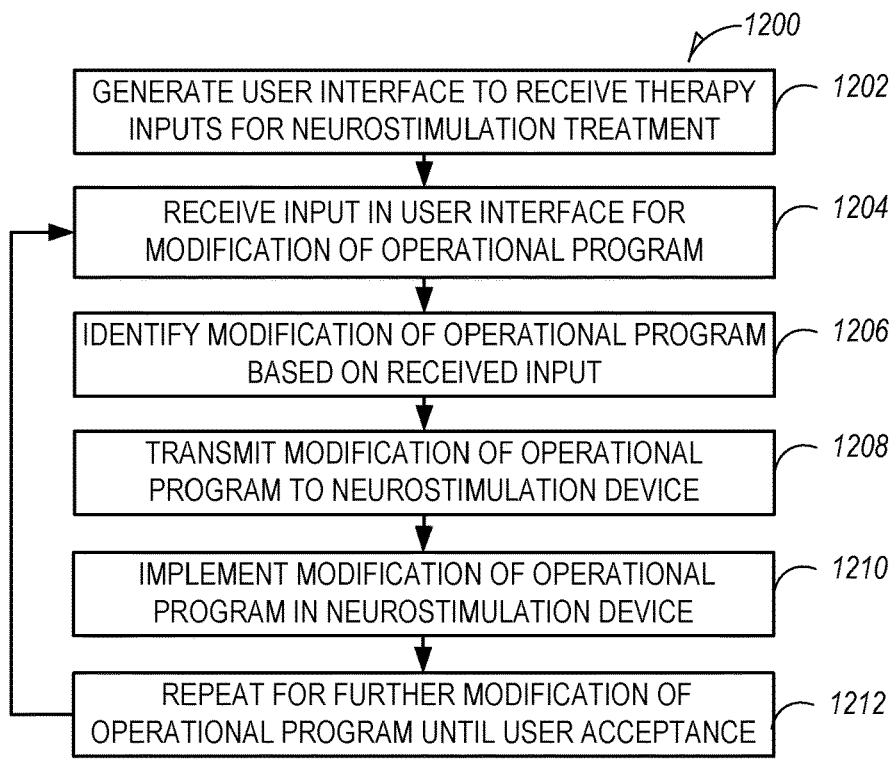
FIG. 12 illustrates, by way of example, an embodiment of a processing method implemented with a patient feedback software application and associated electronic systems.

FIG. 12 illustrates, by way of example, an embodiment of a processing method 1200 implemented with a patient feedback software application and associated electronic systems. For example, the processing method 1200 can be embodied by electronic operations performed by one or more computing systems or devices that are specially programmed to implement and respond to the patient feedback user interface described herein.

For example, the method 1200 includes the generation of a user interface in the patient feedback software application to receive therapy inputs for a neurostimulation treatment (or series of treatments) (operation 1204). This user interface may correspond to the graphical user interface 800 indicated above for FIG. 8, although other formats and styles of a user interface may be used. The method 1200 continues with the receipt of input in the patient feedback user interface, the input including the characteristics of modification of the operational program (operation 1202) such as therapy efficacy indications relating to perceived feeling, perceived location of treatment, perceived pain levels, and user indications whether to keep or disregard the treatment.

The patient feedback software application processes the user input to identify and determine a modification to a characteristic of the neurostimulator program, based on the therapy efficacy input received in the patient feedback user interface (operation 1206). The patient feedback software application may invoke or access associated algorithms of program modification logic to determine an appropriate setting modification based on patient input, device characteristics, safety guidelines, estimated efficacy, and the like.

In response to the identification or determination of the modification for the neurostimulation program, the program data (e.g., updated settings for a program) for the neurostimulation program may be transmitted to the neurostimulation device (operation 1208). This programming may be transmitted directly from a user interface device, transmitted via an intermediate patient programming device, or transmitted via other mechanisms. In response to receipt of the program data, an updated treatment is implemented in the neurostimulation device (operation 1210), such as by updating a setting of an ongoing treatment program.

In response to the transmission of the modification of the operational program, a new operational program will begin operating with the neurostimulation device. The operations may be repeated to allow further modification until the receipt of user acceptance (operation 1212), such as the receipt of additional input in the user interface in response to the change to the neurostimulation treatment (operation 1204), identification of a subsequent modification to the subsequent program based on the received input (operation 1206), transmission of the subsequent program to the neurostimulation device (operation 1208), and implementation of the subsequent program (operation 1212). Other variations to repeat the operations, feedback, and program modifications may also be utilized.

Figure 13:
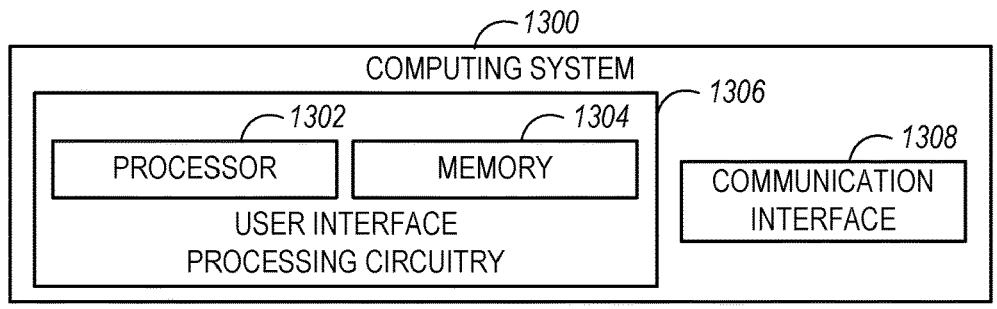
FIG. 13 illustrates, by way of example, a block diagram of an embodiment of a computing system for implementing a patient feedback user interface.

FIG. 13 illustrates, by way of example, a block diagram of an embodiment of a system 1300 (e.g., a computing system) for implementing a patient feedback user interface. The system 1300 may be a remote control device, patient programmer device, or other external device used by a patient, including an unregulated device (e.g., off-the-shelf PC or tablet) used for executing software to output a graphical user interface and receive input for the graphical user interface. In some examples, the system 1300 may be a networked device connected via a network (or combination of networks) to a programming device or programming service using a communication interface 1308, with the programming device or programming service providing output content for the graphical user interface or responding to input of the graphical user interface. The network may include local, short-range, or long-range networks, such as Bluetooth, cellular, IEEE 802.11 (Wi-Fi), or other wired or wireless networks.

The system 1300 includes a processor 1302 and a memory 1304, which can be optionally included as part of user interface processing circuitry 1306. The processor 1302 may be any single processor or group of processors that act cooperatively. The memory 1304 may be any type of memory, including volatile or non-volatile memory. The memory 1304 may include instructions, which when executed by the processor 1302, cause the processor 1302 to implement the features of the user interface, or to enable other features of the user interface processing circuitry 1306. Thus, electronic operations in the system 1300 may be performed by the processor 1302 or the circuitry 1306.

For example, the processor 1302 or circuitry 1306 may implement any of the features of the method 1200 (including operations 1202, 1204, 1206, 1208) to generate a user interface, receive input in a user interface, execute an algorithm or logic to identify a modification of a neurostimulation program, and transmit a modification of the operational program. The processor 1302 or circuitry 1306 may further transmit the modification of the operational program directly to a neurostimulation device (or to a programming device or system that in turn communicates and implements the modification to the neurostimulation device). It will be understood that the processor 1302 or circuitry 1306 may also implement features of the methods 1000 and 1100, and other aspects of the user interfaces described above with reference to FIGS. 6-12.

Figure 14:
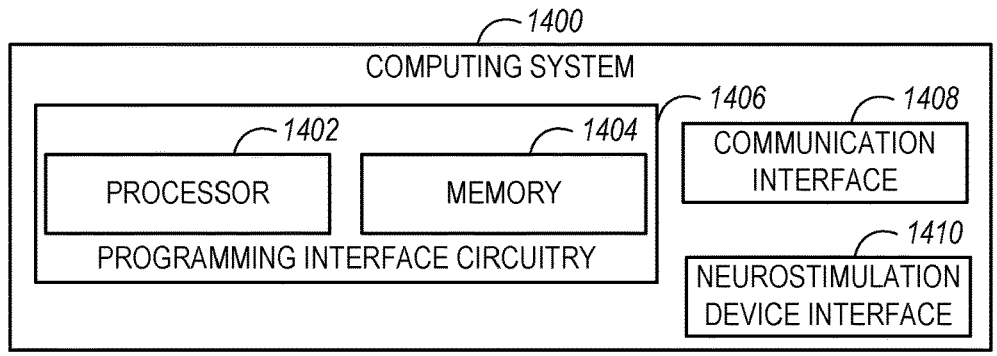
FIG. 14 illustrates, by way of example, a block diagram of an embodiment of a computing system for implementing a programming device.

FIG. 14 illustrates, by way of example, a block diagram of an embodiment of a system 1400 (e.g., a computing system) for implementing a programming device. The system 1400 may be operated by a clinician, a patient, a caregiver, a medical facility, a research institution, a medical device manufacturer or distributor, and embodied in a number of different computing platforms. The system 1400 may be a remote control device, patient programmer device, or other external device used by a patient, including a regulated device used to receive input from a patient feedback user interface and implement programming commands and modification with a neurostimulation device. In some examples, the system 1400 may be a networked device connected via a network (or combination of networks) to a computing system operating a patient feedback user interface computing system using a communication interface 1408, with the patient feedback user interface computing system providing a therapy efficacy indication for the modification of a neurostimulation treatment. The network may include local, short-range, or long-range networks, such as Bluetooth, cellular, IEEE 802.11 (Wi-Fi), or other wired or wireless networks.

The system 1400 includes a processor 1402 and a memory 1404, which can be optionally included as part of programming interface circuitry 1406. The processor 1402 may be any single processor or group of processors that act cooperatively. The memory 1404 may be any type of memory, including volatile or non-volatile memory. The memory 1404 may include instructions, which when executed by the processor 1402, cause the processor 1402 to implement the features of the programming device, or to enable other features of the programming modification logic and programming logic circuitry 1406. Thus, the following references to electronic operations in the system 1400 may be performed by the processor 1402 or the circuitry 1406.

For example, the processor 1402 or circuitry 1406 may implement any of the features of the method 1200 (including operations 1208, 1210) to transmit a modification of the operational program to the neurostimulation device, and implement (e.g., save, persist, activate, control) the modification of the operational program in the neurostimulation device, such as with use of a neurostimulation device interface 1410. The processor 1402 or circuitry 1406 may further provide data and commands to assist the processing and communication of the modification of the operational program from a user interface device (e.g., system 1300) using communication interface 1408. It will be understood that the processor 1402 or circuitry 1406 may also implement features of the methods 1000 and 1100, and other aspects of the programming devices and device interfaces described above with reference to FIGS. 6-12.

Figure 15:
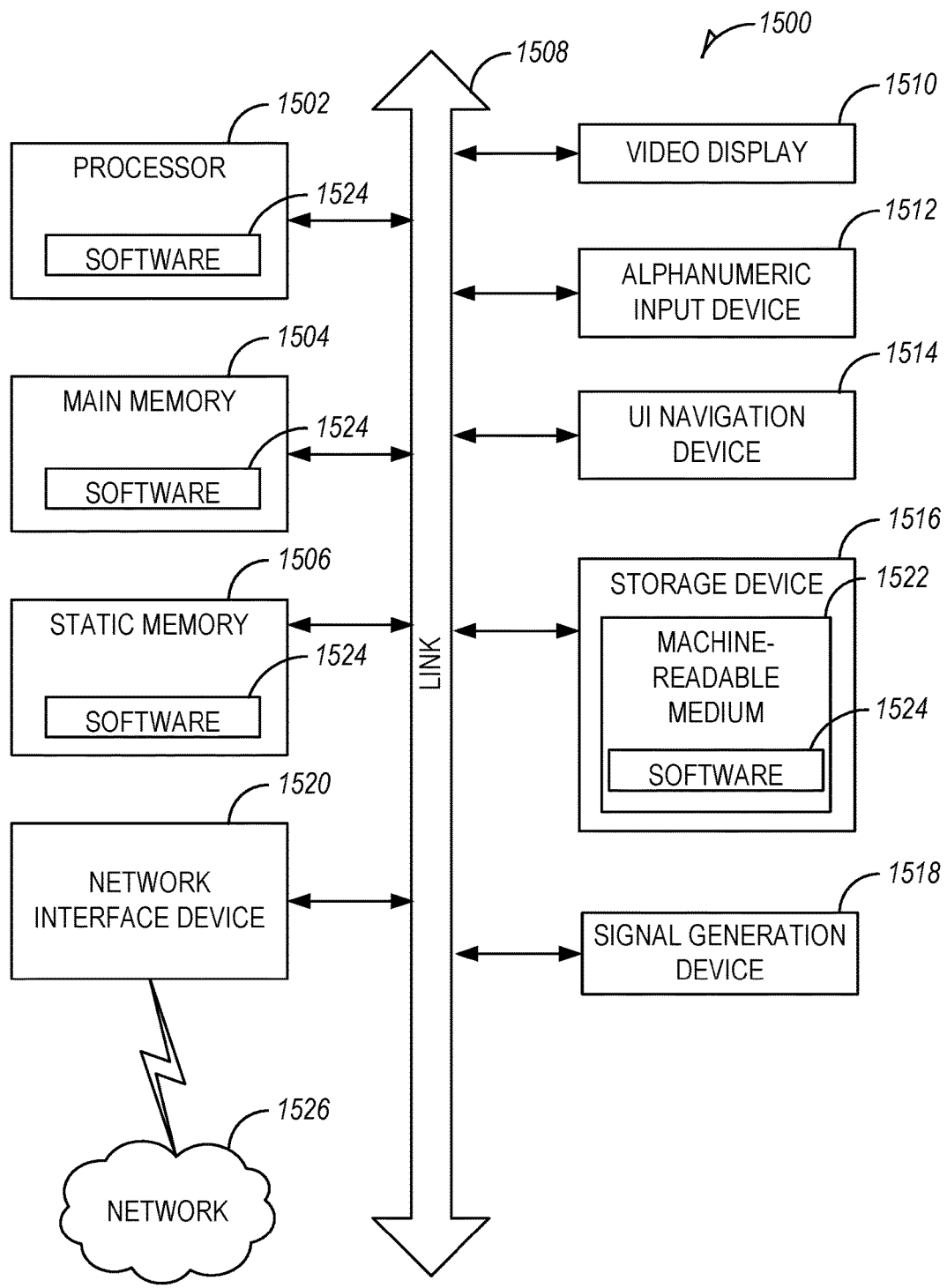
FIG. 15 is a block diagram illustrating a machine in the example form of a computer system, within which a set or sequence of instructions may be executed to cause the machine to perform any one of the methodologies discussed herein, according to an example embodiment.

FIG. 15 is a block diagram illustrating a machine in the example form of a computer system 1500, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 1500 includes at least one processor 1502 (e.g., a central processing unit (CPU), a graphics processing unit (GPU) or both, processor cores, compute nodes, etc.), a main memory 1504 and a static memory 1506, which communicate with each other via a link 1508 (e.g., bus). The computer system 1500 may further include a video display unit 1510, an alphanumeric input device 1512 (e.g., a keyboard), and a user interface (UI) navigation device 1514 (e.g., a mouse). In one embodiment, the video display unit 1510, input device 1512 and UI navigation device 1514 are incorporated into a touch screen display. The computer system 1500 may additionally include a storage device 1516 (e.g., a drive unit), a signal generation device 1518 (e.g., a speaker), a network interface device 1520, and one or more sensors (not shown), such as a global positioning system (GPS) sensor, compass, accelerometer, or other sensor. It will be understood that other forms of machines or apparatuses (such as IPG, RC, CP devices, and the like) that are capable of implementing the methodologies discussed in this disclosure may not incorporate or utilize every component depicted in FIG. 15 (such as a GPU, video display unit, keyboard, etc.).

The storage device 1516 includes a machine-readable medium 1522 on which is stored one or more sets of data structures and instructions 1524 (e.g., software) embodying or utilized by any one or more of the methodologies or functions described herein. The instructions 1524 may also reside, completely or at least partially, within the main memory 1504, static memory 1506, and/or within the processor 1502 during execution thereof by the computer system 1500, with the main memory 1504, static memory 1506, and the processor 1502 also constituting machine-readable media.

While the machine-readable medium 1522 is illustrated in an example embodiment to be a single medium, the term "machine-readable medium" may include a single medium or multiple media (e.g., a centralized or distributed database, and/or associated caches and servers) that store the one or more instructions 1524. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1524 may further be transmitted or received over a communications network 1526 using a transmission medium via the network interface device 1520 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A device, comprising:
    user interface processing circuitry, implemented with a processor and a memory, the user interface processing circuitry to perform electronic operations with the device to:
        generate a user interface to receive a therapy efficacy indication from a human subject for a neurostimulation treatment provided to the human subject, wherein the neurostimulation treatment is provided to the human subject from a neurostimulation device operating with a program of a plurality of programmable parameter settings;
        receive user input in the user interface from the human subject, wherein the user input corresponds to a selection of the therapy efficacy indication from among a plurality of selectable indications output in the user interface, wherein the therapy efficacy indication received from the human subject indicates a perceived stimulation intensity, a perceived pain level, and a perceived location efficacy measurement of the neurostimulation treatment, as perceived by the human subject from the neurostimulation treatment, and wherein the perceived location efficacy measurement provides user feedback that indicates a measurement of proximity and a direction of movement of the neurostimulation treatment in an ongoing treatment area relative to a patient-desired treatment area;
        identify, based on the therapy efficacy indication selected in the user interface, a modification to the program, wherein the modification to the program provides an updated setting for at least one of the plurality of programmable parameter settings, wherein the updated setting includes an updated location for application of the neurostimulation treatment to move towards the desired treatment area, and wherein the updated location is identified based on the perceived location efficacy measurement, with the updated location for the desired treatment area being dynamically determined from the user feedback that indicates the measurement of proximity and the direction of movement of the neurostimulation treatment in the ongoing treatment area; and
        transmit, to the neurostimulation device, the updated setting for the at least one of the plurality of programmable parameter settings, wherein the neurostimulation device modifies the program and implements a change to the neurostimulation treatment in response to receipt of the updated setting, wherein the change to the neurostimulation treatment causes a change of a location of the neurostimulation treatment to the updated location.

2. The device of claim 1, the user interface processing circuitry to further perform electronic operations with the device to:
- receive user input in the user interface to accept the modification to the program, wherein the modification to the program is persisted to the neurostimulation device in response to the user input to accept the modification; and
- wherein the perceived location efficacy measurement is provided from the user input indicating a level of the proximity of the ongoing treatment area relative to the patient-desired treatment area, the proximity being indicated as: far away from the desired treatment area, moving closer to the desired treatment area, or in proximity to the desired treatment area.

3. The device of claim 1,
- wherein the perceived location efficacy measurement provided in the therapy efficacy indication received from the human subject indicates that the neurostimulation treatment is not in proximity to the desired treatment area; and
- wherein the operations to identify the updated location for the modification to the program include:
  - identification of a central point of stimulation based on a pain area of the human subject and therapy characteristics for treatment of the pain area; and
  - identification of a midline for stimulation in the pain area; and
- wherein the modification to the program uses the updated setting to move the neurostimulation treatment to the updated location, the updated location corresponding to the central point of stimulation and the midline for stimulation.

4. The device of claim 3, the user interface processing circuitry to further perform electronic operations with the device to:
- receive user input in the user interface to select a subsequent therapy efficacy indication, wherein the subsequent therapy efficacy indication received from the human subject indicates at least one of: a subsequent perceived stimulation intensity, a subsequent perceived pain level, and a subsequent perceived location efficacy measurement of the neurostimulation treatment, as perceived by the human subject for the modification to the program;
- identify, based on the subsequent therapy efficacy indication selected in the user interface, a subsequent modification to the program, wherein the subsequent modification causes a change to a subsequent updated location of the neurostimulation treatment based on the midline for stimulation in the pain area; and
- repeat operations to receive the subsequent therapy efficacy indication and identify the subsequent modification to the program, until acceptance of the subsequent modification to the program by the human subject.

5. The device of claim 1,
- wherein the perceived location efficacy measurement included in the therapy efficacy indication received from the human subject indicates that the neurostimulation treatment is in proximity to the desired treatment area;
- wherein the operations to identify the modification to the program include: identification of a central point of stimulation using electrode fractionalization; and
- wherein the modification to the program provides the updated setting for at least one of the plurality of programmable parameter settings to move the neurostimulation treatment to the updated location, the updated location corresponding to the central point of stimulation.

6. The device of claim 5, the user interface processing circuitry to further perform electronic operations with the device to:
- receive user input in the user interface to select a subsequent therapy efficacy indication, wherein the subsequent therapy efficacy indication received from the human subject indicates at least one of: a subsequent perceived stimulation intensity, a subsequent perceived pain level, and a subsequent perceived location efficacy measurement of the neurostimulation treatment, as perceived by the human subject for the modification to the program;
- identify, based on the subsequent therapy efficacy indication selected in the user interface, a subsequent modification to the program, wherein the subsequent modification causes a change to a subsequent updated location of the neurostimulation treatment based on the central point of stimulation; and
- repeat operations to receive the subsequent therapy efficacy indication and identify the subsequent modification until acceptance of the subsequent modification to the program by the human subject.

7. The device of claim 1,
- wherein the plurality of programmable parameter settings include settings for one or more of: pulse patterns, pulse shapes, a spatial location of pulses, waveform shapes, or a spatial location of waveform shapes, for modulated energy provided with a plurality of leads of the neurostimulation device.

8. The device of claim 1, the user interface processing circuitry to further perform electronic operations with the device to:
- receive additional user input in the user interface, wherein the additional user input corresponds to an additional selection of an additional therapy efficacy indication by the human subject from among the plurality of selectable indications presented in the user interface, wherein the additional selection of the therapy efficacy indication is provided by the human subject in response to the change to the neurostimulation treatment;
- identify, based on the therapy efficacy indication selected in the user interface, a subsequent updated setting for the at least one of the plurality of programmable parameter settings; and
- transmit, to the neurostimulation device, the subsequent updated setting for the at least one of the plurality of programmable parameter settings, wherein the neurostimulation device modifies the program and implements a change to the neurostimulation treatment in response to receipt of the subsequent updated setting.

9. The device of claim 1, the user interface processing circuitry to further perform electronic operations with the device to:
- receive additional user input in the user interface, wherein the additional user input corresponds to an additional selection of an additional therapy efficacy indication by the human subject from among the plurality of selectable indications presented in the user interface, wherein the additional selection of the therapy efficacy indication is provided by the human subject in response to the change to the neurostimulation treatment;
- identify, based on the therapy efficacy indication selected in the user interface, a subsequent program of the plurality of programmable parameter settings; and transmit, to the neurostimulation device, the subsequent program of the plurality of programmable parameter settings, wherein the neurostimulation device implements a change to the neurostimulation treatment using the subsequent program in response to receipt of the subsequent program.

10. A method, comprising a plurality of electronic operations executed with a processor and memory of a computer system, the plurality of electronic operations including:
generating a user interface to receive a therapy efficacy indication from a human subject for a neurostimulation treatment provided to the human subject, wherein the neurostimulation treatment is provided to the human subject from a neurostimulation device operating with a program of a plurality of programmable parameter settings;
receiving user input in the user interface from the human subject, wherein the user input corresponds to a selection of the therapy efficacy indication from among a plurality of selectable indications output in the user interface, wherein the therapy efficacy indication received from the human subject indicates a perceived stimulation intensity, a perceived pain level, and a perceived location efficacy measurement of the neurostimulation treatment, as perceived by the human subject from the neurostimulation treatment, and wherein the perceived location efficacy measurement provides user feedback that indicates a measurement of proximity and a direction of movement of the neurostimulation treatment in an ongoing treatment area relative to a patient-desired treatment area;
identifying, based on the therapy efficacy indication selected in the user interface, a modification to the program, wherein the modification to the program provides an updated setting for at least one of the plurality of programmable parameter settings, wherein the updated setting includes an updated location for application of the neurostimulation treatment to move towards the desired treatment area, and wherein the updated location is identified based on the perceived location efficacy measurement, with the updated location for the desired treatment area being dynamically determined from the user feedback that indicates the measurement of proximity and the direction of movement of the neurostimulation treatment in the ongoing treatment area; and
transmitting, to the neurostimulation device, the updated setting for the at least one of the plurality of programmable parameter settings, wherein the neurostimulation device modifies the program and implements a change to the neurostimulation treatment in response to receipt of the updated setting, wherein the change to the neurostimulation treatment causes a change of a location of the neurostimulation treatment to the updated location.

11. The method of claim 10, the electronic operations further including:
receiving user input in the user interface to accept the modification to the program, wherein the modification to the program is persisted to the neurostimulation device in response to the user input to accept the modification; and
wherein the perceived location efficacy measurement is provided from the user input indicating a level of the proximity of the ongoing treatment area relative to the patient-desired treatment area, the proximity being indicated as: far away from the desired treatment area, moving closer to the desired treatment area, or in proximity to the desired treatment area.

12. The method of claim 10,
wherein the perceived location efficacy measurement provided in the therapy efficacy indication received from the human subject indicates that the neurostimulation treatment is not in proximity to the desired treatment area; and
wherein the identifying the updated location for the modification to the program includes:
identification of a central point of stimulation based on a pain area of the human subject and therapy characteristics for treatment of the pain area; and
identification of a midline for stimulation in the pain area; and
wherein the modification to the program uses the updated setting to move the neurostimulation treatment to the updated location, the updated location corresponding to the central point of stimulation and the midline for stimulation.

13. The method of claim 12, the electronic operations further including:
receiving user input in the user interface to select a subsequent therapy efficacy indication, wherein the subsequent therapy efficacy indication received from the human subject indicates at least one of: a subsequent perceived stimulation intensity, a subsequent perceived pain level, and a subsequent perceived location efficacy measurement of the neurostimulation treatment, as perceived by the human subject for the modification to the program;
identifying, based on the subsequent therapy efficacy indication selected in the user interface, a subsequent modification to the program, wherein the subsequent modification causes a change to a subsequent updated location of the neurostimulation treatment based on the midline for stimulation in the pain area; and
repeating operations to receive the subsequent therapy efficacy indication and identify the subsequent modification to the program, until acceptance of the subsequent modification to the program by the human subject.

14. The method of claim 10,
wherein the perceived location efficacy measurement included in the therapy efficacy indication received from the human subject indicates that the neurostimulation treatment is in proximity to the desired treatment area;
wherein identifying the modification to the program includes: identification of a central point of stimulation using electrode fractionalization; and
wherein the modification to the program provides the updated setting for at least one of the plurality of programmable parameter settings to move the neurostimulation treatment to the updated location, the updated location corresponding to the central point of stimulation.

15. The method of claim 14, the electronic operations further including:
receiving user input in the user interface to select a subsequent therapy efficacy indication, wherein the subsequent therapy efficacy indication received from the human subject indicates at least one of: a subsequent perceived stimulation intensity, a subsequent perceived pain level, and a subsequent perceived location efficacy measurement of the neurostimulation treatment, as perceived by the human subject for the modification to the program;

identifying, based on the subsequent therapy efficacy indication selected in the user interface, a subsequent modification to the program, wherein the subsequent modification causes a change to a subsequent updated location of the neurostimulation treatment based on the central point of stimulation; and repeating operations to receive the subsequent therapy efficacy indication and identify the subsequent modification until acceptance of the subsequent modification to the program by the human subject.

16. The method of claim 10, wherein the plurality of programmable parameter settings include settings for one or more of: pulse patterns, pulse shapes, a spatial location of pulses, waveform shapes, or a spatial location of waveform shapes, for modulated energy provided with a plurality of leads of the neurostimulation device.

17. The method of claim 10, the electronic operations further including:

receiving additional user input in the user interface, wherein the additional user input corresponds to an additional selection of an additional therapy efficacy indication by the human subject from among the plurality of selectable indications presented in the user interface, wherein the additional selection of the therapy efficacy indication is provided by the human subject in response to the change to the neurostimulation treatment;

identifying, based on the therapy efficacy indication selected in the user interface, a subsequent updated setting for the at least one of the plurality of programmable parameter settings; and transmitting, to the neurostimulation device, the subsequent updated setting for the at least one of the plurality of programmable parameter settings, wherein the neurostimulation device modifies the program and implements a change to the neurostimulation treatment in response to receipt of the subsequent updated setting.

18. The method of claim 11, the electronic operations further including:

receiving additional user input in the user interface, wherein the additional user input corresponds to an additional selection of an additional therapy efficacy indication by the human subject from among the plurality of selectable indications presented in the user interface, wherein the additional selection of the therapy efficacy indication is provided by the human subject in response to the change to the neurostimulation treatment;

identifying, based on the therapy efficacy indication selected in the user interface, a subsequent program of the plurality of programmable parameter settings; and transmitting, to the neurostimulation device, the subsequent program of the plurality of programmable parameter settings, wherein the neurostimulation device implements a change to the neurostimulation treatment using the subsequent program in response to receipt of the subsequent program.

19. At least one non-transitory machine-readable medium including instructions, which when executed by a computing machine, cause the computing machine to:

generate a user interface to receive a therapy efficacy indication from a human subject for a neurostimulation treatment provided to the human subject, wherein the neurostimulation treatment is provided to the human subject from a neurostimulation device operating with a program of a plurality of programmable parameter settings;

receive user input in the user interface from the human subject, wherein the user input corresponds to a selection of the therapy efficacy indication from among a plurality of selectable indications output in the user interface, wherein the therapy efficacy indication received from the human subject indicates a perceived stimulation intensity, a perceived pain level, and a perceived location efficacy measurement of the neurostimulation treatment, as perceived by the human subject from the neurostimulation treatment, and wherein the perceived location efficacy measurement provides user feedback that indicates a measurement of proximity and a direction of movement of the neurostimulation treatment in an ongoing treatment area relative to a patient-desired treatment area;

identify, based on the therapy efficacy indication selected in the user interface, a modification to the program, wherein the modification to the program provides an updated setting for at least one of the plurality of programmable parameter settings, wherein the updated setting includes an updated location for application of the neurostimulation treatment to move towards the desired treatment area, and wherein the updated location is identified based on the perceived location efficacy measurement, with the updated location for the desired treatment area being dynamically determined from the user feedback that indicates the measurement of proximity and the direction of movement of the neurostimulation treatment in the ongoing treatment area; and transmit, to the neurostimulation device, the updated setting for the at least one of the plurality of programmable parameter settings, wherein the neurostimulation device modifies the program and implements a change to the neurostimulation treatment in response to receipt of the updated setting, wherein the change to the neurostimulation treatment causes a change of a location of the neurostimulation treatment to the updated location.

20. The non-transitory machine-readable medium of claim 19, the instructions further to cause the computing machine to:

receive user input in the user interface to accept the modification to the program, wherein the modification to the program is persisted to the neurostimulation device in response to the user input to accept the modification; and wherein the perceived location efficacy measurement is provided from the user input indicating a level of the proximity of the ongoing treatment area relative to the patient-desired treatment area, the proximity being indicated as: far away from the desired treatment area, moving closer to the desired treatment area, or in proximity to the desired treatment area.

* * * * *